(12) United States Patent
Wada et al.

(10) Patent No.: US 7,825,169 B2
(45) Date of Patent: Nov. 2, 2010

(54) WATER-ABSORBENT COMPOSITION, PROCESS FOR PRODUCTION THEREOF, ABSORBENT AND ABSORBING PRODUCT

(75) Inventors: Katsuyuki Wada, Himeji (JP); Hiroko Ueda, Himeji (JP); Kunihiko Ishizaki, Suita (JP); Yoshio Irie, Himeji (JP); Yasuhisa Nakashima, Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 10/448,456

(22) Filed: May 30, 2003

(65) Prior Publication Data

US 2004/0048955 A1   Mar. 11, 2004

(30) Foreign Application Priority Data

Jun. 6, 2002 (JP) .............................. 2002-165979
Sep. 11, 2002 (JP) .............................. 2002-265858

(51) Int. Cl.
  *A61L 9/013* (2006.01)
(52) U.S. Cl. ................. 523/102; 524/78; 524/108; 524/291; 604/359; 604/365; 604/366; 604/367; 604/372
(58) Field of Classification Search ............... 524/78, 524/108, 291, 359; 604/359, 365–367, 372; 523/102, 192
See application file for complete search history.

(56) References Cited

U.S. PATENT DOCUMENTS

| | | | |
|---|---|---|---|
| 4,093,776 A | 6/1978 | Aoki et al. | |
| 4,286,082 A | 8/1981 | Tsubakimoto et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,873,299 A | 10/1989 | Nowakowsky et al. | |
| 4,972,019 A * | 11/1990 | Obayashi et al. | 524/83 |
| 4,973,632 A | 11/1990 | Nagasuna et al. | |
| 4,985,518 A | 1/1991 | Alexander et al. | |
| 5,124,416 A | 6/1992 | Haruna et al. | |
| 5,145,906 A | 9/1992 | Chambers et al. | |
| 5,244,735 A | 9/1993 | Kimura et al. | |
| 5,250,640 A | 10/1993 | Irie et al. | |
| 5,264,495 A | 11/1993 | Irie et al. | |
| 5,380,808 A | 1/1995 | Sumiya et al. | |
| 5,422,405 A * | 6/1995 | Dairoku et al. | 525/384 |
| 5,797,893 A | 8/1998 | Wada et al. | |
| 5,980,879 A | 11/1999 | Hiroki et al. | |
| 6,071,976 A | 6/2000 | Dairoku et al. | |
| 6,228,930 B1 | 5/2001 | Dairoku et al. | |
| 6,254,990 B1 | 7/2001 | Ishizaki et al. | |
| 6,350,812 B1 * | 2/2002 | Vert et al. | 524/845 |
| 6,469,080 B2 | 10/2002 | Miyake et al. | |
| 6,562,879 B1 | 5/2003 | Hatsuda et al. | |
| 6,800,789 B2 * | 10/2004 | Kasai et al. | 604/367 |

| | | | |
|---|---|---|---|
| 2002/0013394 A1 * | 1/2002 | Dairoku et al. | 524/109 |
| 2003/0004479 A1 | 1/2003 | Ueda et al. | |
| 2003/0065087 A1 * | 4/2003 | Nambu et al. | 524/588 |
| 2003/0208173 A1 * | 11/2003 | Lagerstedt-Eidrup et al. | 604/367 |

FOREIGN PATENT DOCUMENTS

| | | |
|---|---|---|
| CA | 2333131 | 11/2000 |
| EP | 629411 | 6/1994 |
| EP | 0 604 961 A2 | 7/1994 |
| EP | 0 712 659 A1 | 5/1996 |
| EP | 0 811 636 A1 | 12/1997 |
| EP | 0 838 466 A2 | 4/1998 |
| EP | 0 922 717 A1 | 6/1999 |
| EP | 0 955 086 A2 | 11/1999 |
| EP | 0 995 753 A2 | 4/2000 |
| EP | 1 099 474 A1 | 5/2001 |
| JP | 59-115741 | 7/1984 |
| JP | 60-158861 | 8/1985 |
| JP | 63-135501 | 6/1988 |
| JP | 1-195855 A | 8/1989 |
| JP | 02-041155 | 2/1990 |
| JP | 03-059075 | 3/1991 |
| JP | 3-268751 A | 11/1991 |
| JP | 04-139104 | 5/1992 |
| JP | 05-179053 | 7/1993 |
| JP | 07-165981 | 6/1995 |
| JP | 7-228790 A | 8/1995 |
| JP | 09-208787 | 8/1997 |
| JP | 11-116829 | 4/1999 |
| JP | 2938507 | 6/1999 |
| JP | 11-241030 | 9/1999 |
| JP | 2000-51339 | 2/2000 |
| JP | 2000-51399 | 2/2000 |
| JP | 2000-302876 A | 10/2000 |

(Continued)

*Primary Examiner*—Peter Szekely
(74) *Attorney, Agent, or Firm*—Nixon & Vanderhye PC

(57) ABSTRACT

A water-absorbent composition includes: a specific plant extract; a water-absorbent resin whose surface portion and/or periphery thereof is treated; and/or a water-absorbent resin having a specific property. Specifically, it is preferable to use a water-absorbent resin having three characteristics: (1) a specific neutralization rate, (2) a specific particle diameter, and (3) a specific plant extract. The water-absorbent composition has a superior deodorant performance and an absorbent characteristic when the water-absorbent composition is used (provided) in an absorbing product such as a paper diaper, thereby providing a superior deodorant performance and a superior absorbent characteristic to the foregoing absorbing product.

13 Claims, 3 Drawing Sheets

FOREIGN PATENT DOCUMENTS

| | | |
|---|---|---|
| JP | 2000-342963 A | 12/2000 |
| JP | 3078388 U | 4/2001 |
| JP | 2001-258934 A | 9/2001 |
| JP | 2002-88687 A | 3/2002 |
| WO | WO 96/27435 | 9/1996 |
| WO | 0001479 (A1) | 1/2000 |
| WO | WO 00/35923 | 6/2000 |
| WO | WO 01/41819 A1 | 6/2001 |
| WO | 0242379 (A1) | 5/2002 |

* cited by examiner

WATER-ABSORBENT COMPOSITION, PROCESS FOR PRODUCTION THEREOF, ABSORBENT AND ABSORBING PRODUCT

FIELD OF THE INVENTION

The present invention relates to a water-absorbent composition, a process for production thereof, an absorbent, and an absorbing product. In further detail, the present invention relates to a water-absorbent resin composition, a process for production thereof, an absorbent, and an absorbing product, which have a particularly superior deodorant performance and a stable absorbent characteristic when they are used for an absorbent of a sanitary material such as a paper diaper, a sanitary napkin, and an incontinence pad, so that it is possible to provide particularly a superior deodorant performance and a superior absorbent characteristic to the sanitary material.

BACKGROUND OF THE INVENTION

In recent years, water-absorbent resins for absorbing body fluids (urine and blood) are widely used as one of constituent elements (a main constituent element) of a sanitary material (absorbing product) such as a paper diaper, a sanitary napkin, and an incontinence pad.

Known water-absorbent resins include, for example, partially neutralized and cross-linked polyacrylic acid, hydrolyzed starch-acrylonitrile graft polymer, neutralized starch-acrylic acid graft polymer, saponified vinyl acetate-acrylic ester copolymer, cross-linked carboxymethyl cellulose, hydrolyzed acrylonitrile copolymer or acrylamide copolymer, or cross-linked acrylonitrile copolymer or acrylamide copolymer, cross-linked cationic monomer, cross-linked isobutylene-maleic acid copolymer, and cross-linked copolymer of 2-acrylamido-2-methylpropane sulfonic acid and acrylic acid.

The water-absorbent resin has been conventionally desired to have the following absorbent characteristics: a high absorption capacity, a high absorption rate, liquid permeability, gel strength of swelling gel, an absorbent amount at which water is absorbed from a base material containing aqueous fluids, and the like, when the water-absorbent resin comes into contact with aqueous fluids such as body fluids.

Further, the water-absorbent resin used in a diaper, particularly in an adult diaper, is required to have not only the aforementioned absorbent characteristics but also a deodorant characteristic as an additional function.

Conventionally, various kinds of study have been performed so as to provide not only the absorbent characteristics but also the additional function to the water-absorbent resin by adding a deodorant and antibacterial compound to the water-absorbent resin.

Then, combinations of various kinds of deodorants and antibacterial agents have been proposed so as to provide the deodorant characteristic to the water-absorbent resin. For example, Patent Document 1 (Japanese Unexamined Patent Publication No. 158861/1985 (Tokukaisho 60-158861) (Publication date: Aug. 20, 1985)) recites a water-absorbent resin composition (absorbent agent) constituted of a water-absorbent resin and a theaceous plant leaf extract. Patent Document 2 (Japanese Unexamined Patent Publication No. 241030/1999 (Tokukaihei 11-241030) (Publication date: Sep. 7, 1999)) recites a water-absorbent resin constituted of a coniferous tree extract and a water-absorbent resin having a specific performance. Patent Document 3 (Japanese Unexamined Patent Publication No. 176338/1996 (Tokukaihei 8-176338) (Publication date: Jul. 9, 1996)) recites a deodorant water-absorbent resin composition in which zeolite particles are dispersed inside a water-absorbent resin compound. Patent Document 4 (Japanese Unexamined Patent Publication No. 51399/2000 (Tokukai 2000-51399) (Publication date: Feb. 22, 2000)) recites a persistent antibacterial deodorant constituted of (a) at least one kind of powder selected from a Japanese horse-radish extract, a mustard extract, and allyl isothiocyanate and (b) a water-absorbent gelatinizer for sustaining the antibacterial deodorant action of the powder. Patent Document 5 (Japanese Unexamined Patent Publication No. 79159/2000 (Tokukai 2000-79159) (Publication date: Mar. 21, 2000)) recites a powdery deodorant/antibacterial water-absorbent resin compound constituted of (a) a water-absorbent resin, (b) a compound having an antibacterial function with respect to an ammonifying bacteria, and (c) a medical agent having neutralizing ability with respect to ammonia, or having neutralizing ability and absorbing ability with respect to ammonia. Patent Document 6 (Japanese Unexamined Patent Publication No. 234087/2001 (Tokukai 2001-234087) Publication date: Aug. 28, 2001)) recites a water-absorbent resin composition in which a specific water-absorbent resin contains a water-soluble deodorant.

Further, techniques for providing the deodorant characteristic to an absorbing product using a water-absorbent resin are known. Patent Document 7 (Japanese Unexamined Patent Publication No. 41155/1990 (Tokukaihei 2-41155) (Publication date: Feb. 9, 1990)) recites an absorbing product containing manufactured tea and a water-absorbent resin. Patent Document 8 (Japanese Unexamined Patent Publication No. 135501/1988 (Tokukaisho 63-135501) (Publication date: Jun. 7, 1988)) recites a disposable diaper in which a water-absorbent resin contains benzalkonium chloride and/or chlorhexidine gluconate.

Further, as other techniques for providing the additional function by adding a deodorant and an antibacterial compound to the water-absorbent resin, techniques recited in the following documents are known. Patent Document 9 (Japanese Unexamined Patent Publication No. 139104/1992 (Tokukaihei 4-139104) (Publication date: May 13, 1992)) recites gelatinous insecticide obtained by making a water-absorbent resin absorb aqueous emulsion made mainly of volatile monoterpene compound. Patent Document 10 (Japanese Unexamined Patent Publication No. 59075/1991 (Tokukaihei 3-59075) (Publication date: Mar. 14, 1991)) recites a method for producing an antibacterial resin compound formed as follows: liquid made by dissolving antibacterial agent in volatile solvent is made to adhere to a water-absorbent resin, and the volatile solvent is removed thereafter, so that an antibacterial coating is formed on a surface of the water-absorbent resin. Patent Document 11 (Japanese Unexamined Patent Publication No. 179053/1993 (Tokukaihei 5-179053) (Publication date: Jul. 20, 1993)) and Patent Document 12 (Japanese Unexamined Patent Publication No. 165981/1995 (Tokukaihei 7-165981) (Publication date: Jun. 27, 1995)) recite a water-absorbent resin containing antibacterial phosphate. Patent Document 13 (Japanese Unexamined Patent Publication No. 116829/1999 (Tokukaihei 11-116829) (Publication date: Apr. 27, 1999)) recites a water-absorbent resin composition made of water-absorbent resin, tannic acid (salt), and complex silicate compound. Patent Document 14 (Japanese Unexamined Patent Publication No. 208787/1997 (Tokukaihei 9-208787) (Publication date: Aug. 12, 1997)) recites a water-absorbent resin composition obtained by internally providing or applying a natural antibacterial element, extracted from a grapefruit seed and/or a herb, to a water-absorbent resin. Patent Document 15 (Japanese Unexamined Patent Publication No. 285021/2002

(Tokukai 2002-285021) (Publication date: Oct. 3, 2002)) recites a particulate water-absorbent resin composition, including a plant powder and a water-absorbent resin whose surface has been treated, which has a deodorant index of not less than 180. Patent Document 16 (international publication pamphlet No. WO99/64485 (Publication date: Dec. 16, 1999)) recites a water-absorbent resin compound obtained by combining cyclodextrin and/or a cyclodextrin derivative to a water-absorbent resin by covalent bond and/or ionic bond. Patent Document 17 (international publication pamphlet No. WO01/41819 (Publication date: Jun. 14, 2001)) recites a water-absorbent resin composition made of water-absorbent resin and silver salt or colloidal silver.

However, although a general deodorant exhibits deodorant effect to some extent by chemically reacting with or absorbing odor elements, a deodorant effect with respect to odor of urine is hardly confirmed. Further, the deodorant cannot prevent microbes or bacteria from decomposing or putrefying organic matters. While, although a general antibacterial agent can prevent odor caused by decomposition or putrefaction, a deodorant effect with respect to odor of urine right after excretion is hardly confirmed. Further, it is general that merely adding a general deodorant compound to the water-absorbent resin may not sufficiently provide a deodorant performance to a whole absorbing product such as a paper diaper when such water-absorbent resin is used in the absorbing product.

Thus, the above-mentioned conventional methods for improving the deodorant characteristic sometimes does not exhibit sufficient effects in practical use, so that the absorbing product using the water-absorbent resin obtained by the conventional methods does not exhibit sufficient effects.

Further, high safety is so desired upon providing the deodorant performance so as to use the water-absorbent resin in an absorbing product and the like.

SUMMARY OF THE INVENTION

Thus, the object of the present invention is to provide a water-absorbent composition, a process for production thereof, an absorbent, and an absorbing product, which have a superior deodorant performance and absorbent characteristic when they are used (provided) in an absorbent of a sanitary material such as a paper diaper, and which can provide a superior deodorant performance and a superior absorbent characteristic to the foregoing absorbing product. The further object of the present invention is to provide a water-absorbent composition, a process for production thereof, an absorbent, and an absorbing product, being highly safe, which have particularly a superior deodorant performance and a superior absorbent characteristic when they are provided in an absorbent of a sanitary material such as a paper diaper, and which can provide a superior deodorant performance and a superior absorbent characteristic to the foregoing absorbing product.

The present inventors earnestly studied a case where absorbent agent is provided in an absorbing product such as a diaper, in view of a superior deodorant characteristic and a superior absorbent characteristic. As a result, they found that the foregoing object can be achieved by a water-absorbent composition made by combining a specific plant extract with a water-absorbent resin whose surface portion and/or a periphery thereof had been treated, and/or a water-absorbent resin having a specific property. The present invention was completed based on these findings.

The aforementioned plant extract contains at least one kind selected from polyphenol, flavones, and caffeine. As the specific plant extract according to the present invention, a semi-fermented tea extract and/or a fermented tea extract (i.e., at least one kind of polyphenol selected from a group of a semi-fermented tea extract and a fermented tea extract) is particularly preferable. As a result of earnest study performed by the present inventors, they found that the foregoing object can be achieved by combining, for example, the semi-fermented tea extract and/or the fermented tea extract with a water-absorbent resin whose surface had been treated and/or a water-absorbent resin having a specific property, so as to provide a specific performance.

That is, the water-absorbent composition of the present invention includes: a semi-fermented tea extract and/or a fermented tea extract; and a water-absorbent resin whose surface portion and/or a periphery thereof has been treated by cross-linking agent.

The water-absorbent composition of the present invention is preferably such that: an absorption capacity (CRC) in case where 0.90 mass % of physiological saline is absorbed without load for 60 minutes is not less than 25 g/g and not more than 60 g/g, and an absorption index under a load is not less than 14 g/g, and an absorption rate is not more than 60 seconds.

Further, an absorbent of the present invention includes the water-absorbent composition of the present invention. It is possible to preferably use the absorbent of the present invention as an absorbent layer of an absorbing product such as a sanitary material for example.

The absorbing product of the present invention includes: an absorbent (absorbent layer) containing the water-absorbent composition of the present invention; a surface sheet having liquid permeability; and a back sheet having liquid impermeability.

The aforementioned water-absorbent composition of the present invention is a new water-absorbent composition which can provide a deodorant function to the absorbing product and exhibits a superior deodorant characteristic and a superior absorbent characteristic. The cause of this has not been clarified, but may be as follows: a semi-fermented tea extract and/or a fermented tea extract is added particularly to a water-absorbent resin having a specific absorption capacity, a specific absorption index under a load, and a specific absorption rate and/or a water-absorbent resin whose surface has been treated, thereby achieving the most suitable balance between action of active elements contained in the semi-fermented tea extract and/or fermented tea extract and liquid absorption when the water-absorbent resin comes into contact with urine.

Further, the absorbent and the absorbing product of the present invention include the water-absorbent composition of the present invention, so that the superior deodorant function of the water-absorbent composition can be provided to the absorbing product. Thus, it is possible to preferably use the absorbing product in a sanitary material such as a paper diaper, a sanitary napkin, an adult incontinence pad, and an adult diaper, and it is possible to keep comfortable feeling in wearing the sanitary material for a long time.

Further, the present inventors earnestly studied a case where the water-absorbent composition (water-absorbent resin composition) is provided in an absorbing product such as a diaper, in view of superior deodorant performance and a superior absorbent characteristic. As a result, they found that the foregoing object can be achieved by a particulate water-absorbent composition (particulate water-absorbent resin composition) having three characteristics: (1) a specific neutralization rate, (2) a specific particle diameter, and (3) a specific plant extract. The present invention was completed based on these findings.

That is, the water-absorbent composition of the present invention is a particulate water-absorbent composition (particulate water-absorbent resin composition) which is made mainly of a water-absorbent resin (A) having a cross-linking structure obtained by polymerizing an unsaturated monomer containing acid groups. The water-absorbent composition is characterized in that: (1) ⅓ to less than ¾ (however, when a plant component (B) described later is selected from a semi-fermented tea extract and/or a fermented tea extract, ⅓ to less than ⅘) of all molar quantities of acid group, preferably ⅓ to ⅔ of all the molar quantities of the acid group are neutralized, and (2) the amount of particles whose particle diameter ranges from less than 850 μm to not less than 150 μm is not less than 90 mass % with respect to the whole and the amount of particles whose particle diameter is not less than 300 μm is not less than 60 mass % with respect to the whole, and (3) a plant component (B) containing at least one kind selected from polyphenol, flavones, and caffeine, is included.

The process of the present invention for producing the water-absorbent composition, being particulate, which is made mainly of a water-absorbent resin (A) having a cross-linking structure obtained by polymerizing an unsaturated monomer containing acid groups, wherein (1) not less than ⅓ and less than ¾ (however, when the plant component (B) described later is selected from the semi-fermented tea extract and/or the fermented tea extract, not less than ⅓ and less than ⅘) of all molar quantities of an acid group is neutralized, and (2) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and (3) a plant component (B) containing at least one kind selected from polyphenol, flavones, and caffeine is included, and the process includes the steps of: polymerizing the unsaturated monomer containing acid groups, in which not less than ⅓ and less than ¾ (however, when the plant component (B) described later is selected from the semi-fermented tea extract and/or the fermented tea extract, not less than ⅓ and less than ⅘) of all molar quantities of the acid group are neutralized, so as to obtain the water-absorbent resin having the cross-linking structure; adjusting a particle size of thus obtained water-absorbent resin so that the amount of the particles whose particle diameter is less than 850 μm and not less than 150 μm is not less than 90 mass % with respect to the whole; and mixing the water-absorbent resin whose particle size has been adjusted with the plant component (B) containing at least one kind selected from polyphenol, flavones, and caffeine.

Further, the absorbent of the present invention includes the water-absorbent composition. It is preferable that the absorbent includes a hydrophilic fiber.

Further, the absorbent of the present invention includes: a water-absorbent composition (particulate water-absorbent resin composition), being particulate, which is made mainly of a water-absorbent resin (A) having a cross-linking structure obtained by polymerizing an unsaturated monomer containing acid groups; and a hydrophilic fiber, wherein the water-absorbent composition is such that: (1) not less than ⅓ and less than ¾ (however, in a case where a plant component (B) described later is selected from a semi-fermented tea extract and/or a fermented tea extract, ⅓ to ⅘), preferably ⅓ to ⅔ of all molar quantities of an acid group is neutralized, and (2) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and the absorbent further includes (3) a plant component (B) containing at least one kind selected from polyphenol, flavones, and caffeine.

Further, the aforementioned absorbing product of the present invention includes: an absorbent; a surface sheet having liquid permeability; and a back sheet having liquid impermeability.

Also the aforementioned water-absorbent composition (water-absorbent resin composition) can provide a deodorant function to the absorbing product, so as to provide a new water-absorbent composition (water-absorbent resin composition) which exhibits a superior deodorant performance and an absorbent characteristic for a long time. Further, according to the process for producing the water-absorbent composition, it is possible to easily obtain the water-absorbent composition arranged in the foregoing manner.

Further, the absorbent and the absorbing product of the present invention exhibit a superior deodorant performance and a stable absorbent characteristic, so that it is possible to preferably use the absorbing product in a sanitary material such as a paper diaper, a sanitary napkin, an adult incontinence pad, and an adult diaper, and it is possible to keep comfortable feeling in wearing the sanitary material for a long time.

For a fuller understanding of the nature and advantages of the invention, reference should be made to the ensuing detailed description taken in conjunction with the accompanying drawings.

DESCRIPTION OF THE EMBODIMENTS

Figure 1:
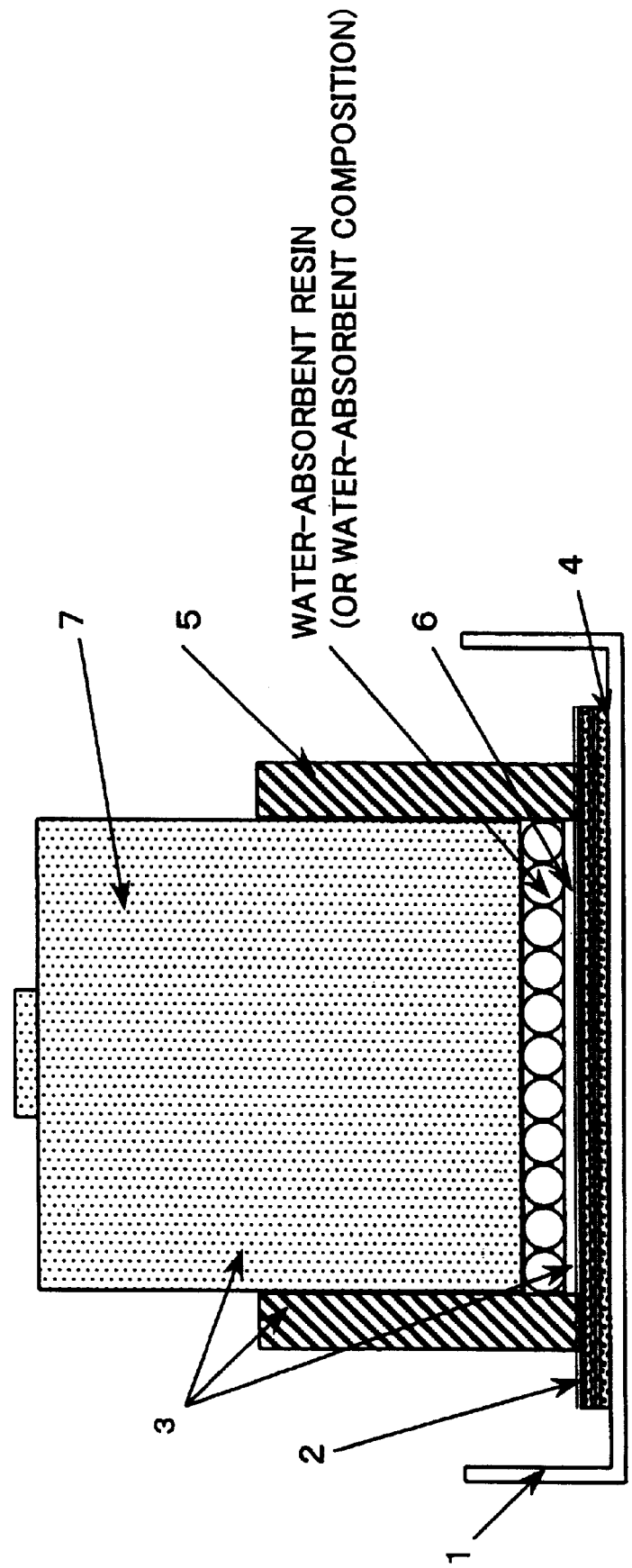
FIG. 1 is a cross sectional view schematically showing a measuring apparatus used in measuring an absorbing power under a load which indicates one performance of the water-absorbent resin.

As described above, the present inventors performed earnest study so as to provide a water-absorbent composition, a process for production thereof, an absorbent, and an absorbing product, which have a superior deodorant performance and absorbent characteristic when they are used (provided) in an absorbent of a sanitary material such as a paper diaper, and which can provide a superior deodorant performance and a superior absorbent characteristic to the foregoing absorbing product, particularly to provide a water-absorbent composition, a process for production thereof, an absorbent, and an absorbing product, being highly safe, which have particularly a superior deodorant performance and a superior absorbent characteristic when they are provided in an absorbent of a sanitary material such as a paper diaper, and which can provide a superior deodorant performance and a superior absorbent characteristic to the foregoing absorbing product. As a result, they found that the foregoing object can be achieved by a water-absorbent composition made by combining a specific plant extract with a water-absorbent resin whose surface has been treated and/or a water-absorbent resin having a specific property, preferably by a water-absorbent composition having three characteristics: (1) a specific neutralization rate, (2)

a specific particle diameter, and (3) a specific plant extract. The present invention was completed based on these findings.

More specifically, the present inventors found that the foregoing object can be achieved by combining a semi-fermented tea extract and/or a fermented tea extract with a water-absorbent resin whose surface has been treated and/or a water-absorbent resin having a specific property, so as to provide a specific performance. Further, the present inventors found it more desirable that: the water-absorbent resin is water-absorbent resin (A) having a cross-linking structure obtained by polymerizing an unsaturated monomer containing acid groups, and a water-absorbent composition made by combining the water-absorbent resin (A) with a semi-fermented tea extract and/or a fermented tea extract is a particulate water-absorbent composition (particulate water-absorbent resin composition) which is made mainly of the water-absorbent resin (A), and the water-absorbent composition has a specific neutralization rate and a specific particle diameter.

Further, as a result of earnest study, the present inventors found the following fact. If the obtained water-absorbent composition is a particulate water-absorbent composition (particulate water-absorbent resin composition) which is made mainly of the water-absorbent resin (A), and the water-absorbent composition has a specific neutralization rate and a specific particle diameter, the water-absorbent composition has a superior deodorant performance and an absorbent characteristic when it is used (provided) in an absorbing product such as a diaper even though the water-absorbent composition contains a plant extract other than the semi-fermented tea extract and/or the fermented tea extract, specifically at least one kind selected from polyphenol, flavones, and caffeine, so that it is possible to provide a superior deodorant performance and a superior absorbent characteristic to the absorbing product. That is, the present inventors found that the foregoing object can be achieved also by the particulate water-absorbent composition (particulate water-absorbent resin composition) having three characteristics: (1) a specific neutralization rate, (2) a specific particle diameter, and (3) a specific plant extract.

The following is detail description thereof.

Embodiment 1

First, description is given on a water-absorbent composition made by combining a semi-fermented tea extract and/or a fermented tea extract with a water-absorbent resin whose surface has been treated and/or water-absorbent resin having a specific property.

In the present embodiment, the water-absorbent resin means polymer whose inside is cross-linked and/or polymer whose inside and surface are cross-linked. Specifically, the water-absorbent resin whose surface has been treated means the polymer whose inside and surface are cross-linked.

The water-absorbent resin used in the present embodiment has the following characteristics (i) and/or (ii):

(i) preferably, its surface portion and/or periphery thereof is treated by cross-linking agent (that is, its surface portion and/or periphery thereof is treated by cross-linking agent which is reactive with a functional group of the water-absorbent resin), and (ii) an absorption capacity (CRC) is not less than 25 g/g and not more than 60 g/g, and an absorption index under a load is not less than 14 g/g, and an absorption rate is not more than 60 seconds. Note that, measuring methods of these values are defined in Examples.

When combining exclusively (a) the water-absorbent resin whose absorption capacity (CRC) is not less than 25 g/g and not more than 60 g/g and absorption index under a load is not less than 14 g/g and absorption rate is not more than 60 seconds with (b) the semi-fermented tea extract and/or the fermented tea extract, this enhances the deodorant performance of the whole diaper, so that such absorbent characteristics are preferable. The cause of this has not been clarified, but may be as follows: a semi-fermented tea extract and/or a fermented tea extract is added particularly to a water-absorbent resin having a specific absorption capacity, a specific absorption index under a load, and a specific absorption rate and/or a water-absorbent resin whose surface has been treated, thereby achieving the most suitable balance between action of active elements contained in the semi-fermented tea extract and/or fermented tea extract and liquid absorption when the water-absorbent resin comes into contact with urine.

The water-absorbent resin, used in the present embodiment, whose surface portion and/or periphery thereof has been treated by a cross-linking agent, is obtained generally by a cross-linking process performed with respect to the surface of the water-absorbent resin.

In the present embodiment, the water-absorbent resin means water swellable/water insoluble cross-linked polymer, and means cross-linked polymer which absorbs water so as to form anionic water insoluble hydrogel, or nonionic water insoluble hydrogel, or cationic water insoluble hydrogel, or mixed water insoluble hydrogel. Further, in the present embodiment, the water-absorbent composition means a water-absorbent material which contains mainly the water-absorbent resin, preferably not less than 70 mass % (weight %) of the water-absorbent resin, more preferably not less than 80 mass % of the water-absorbent resin.

Note that, the water swellable means to absorb a large quantity of water such as not less than twice, preferably 10 to 3000 times, more preferably 50 to 2000 times as large as the dry water-absorbent resin, in ion exchange water, and the water insoluble means that the water extractable of an uncross-linked portion of the water-absorbent resin is not more than 50 mass %, preferably not more than 25 mass %, more preferably not more than 20 mass %, still more preferably not more than 15 mass %, particularly preferably not more than 10 mass %.

A measuring method of the water extractable is recited in EDANA RECOMMENDED TEST METHODS 470, 1-99 EXTRACTABLES of EUROPEAN DISPOSABLES AND NONWOVENS ASSOCIATION.

Examples of such water-absorbent resin include one kind selected from partially neutralized and cross-linked polyacrylic acid, hydrolyzed starch-acrylonitrile graft polymer, neutralized starch-acrylic acid graft polymer, saponified vinyl acetate-acrylic ester copolymer, hydrolyzed acrylonitrile copolymer or acrylamide copolymer, or cross-linked acrylonitrile copolymer or acrylamide copolymer, denaturated polyvinyl alcohol containing a carboxyl group, cross-linked isobutylene-maleic anhydride copolymer, or mixture thereof.

One kind or mixture of the water-absorbent resins are used. Among of them, one kind or mixture of resins containing carboxyl groups are preferably used, and it is preferable that a main constituent is polymer (water swellable polyacrylic (salt) cross-linked polymer) typically obtained by polymerizing and cross-linking a monomer which is made mainly of acrylic acid and/or salt thereof (neutralized acrylic acid). Further, the water-absorbent resin may be hydrous hydro-gel, or may be powder obtained by ordinarily grinding the resin before and/or after drying the resin as required.

The water-absorbent resin is obtained, for example, as follows: after polymerizing or copolymerizing one or more kinds selected from (a) unsaturated carboxylic acids such as (meth)acrylic acid, maleic acid, maleic anhydride, fumaric acid, crotonic acid, itaconic acid, and β-acryloyl oxypropionic acid and (b) neutralized acids thereof, the polymer is ground and classified, and then the particle diameter is adjusted.

A neutralization rate of the acid group is adjusted within a range of preferably from 30 to 100 mol %, more preferably from 50 to 90 mol %, still more preferably from 60 to 90 mol %, further more preferably from 60 to 75 mol %, particularly preferably from 65 to 75 mol %. The acid group may be neutralized as an acid group monomer in aqueous solution before polymerization, or may be neutralized in aqueous solution of the polymer, that is, the acid group may be neutralized by post-neutralizing the polymerized gel, or may be neutralized by both these processes. As salt for neutralization, sodium, lithium, potassium, ammonia, amines are preferably used.

Among the monomers, (meth)acrylic acid and neutralized (meth)acrylic acid are more preferably used. The mass average particle diameter is within a range of preferably from 100 to 600 μm, more preferably from 200 to 500 μm, and the amount of particles whose particle diameter is less than 106 μm is not more than 10 mass %, preferably not more than 5 mass %, more preferably not more than 3 mass %.

Further, the water-absorbent resin may be copolymer obtained by copolymerizing with another monomer which is copolymerizable with the monomer. Examples of another monomer specifically include: anionic unsaturated monomer such as, vinyl sulfonic acid, styrene sulfonic acid, 2-(meth)acrylamido-2-methylpropane sulfonic acid, 2-(meth)acryloylethane sulfonic acid, and 2-(meth)acryloylpropane sulfonic acid, and salts thereof; nonionic unsaturated monomer containing a hydrophilic group, such as acrylamide, methacrylamide, N-ethyl(meth) acrylamide, N-n-propyl (meth) acrylamide, N-isopropyl (meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono (meth)acrylate, vinylpyridine, N-vinylpyrrolidone, N-acryloyl piperidine, and N-acryloyl pyrrolidine; and a cationic unsaturated monomer, such as N,N-dimethylaminoethyl (meth)acrylate, N,N-diethylaminoethyl (meth)acrylate, N,N-dimethylaminopropyl (meth)acrylate, and N,N-dimethylaminopropyl (meth) acrylamide, and quaternary salts thereof.

It is preferable that an inside of the water-absorbent resin is cross-linked by reacting or copolymerizing the water-absorbent resin with a cross-linking agent containing a plurality of polymerizable unsaturated groups or a plurality of reactive groups. Further, the water-absorbent resin may be a self-cross-linking type which requires no cross-linking agent.

Examples of the cross-linking agent (also referred to as an inside cross-linking agent) specifically include N,N'-methylene bis (meth)acrylamide, (poly) ethylene glycol di (meth) acrylate, (poly) propylene glycol di (meth) acrylate, trimethylolpropane di (meth)acrylate, trimethylolpropane tri (meth) acrylate, glycerine tri (meth)acrylate, glycerine acrylate methacrylate, ethyleneoxide denaturated trimethylolpropane tri (meth)acrylate, pentaerythriotol tetra (meth)acrylate, dipentaerythritol hexa (meth)acrylate, triallyl cyanurate, triallyl isocyanurate, triallyl phosphate, triallylamine, poly (meth)allyloxy alkane, (poly) ethylene glycol diglycidyl ether, glycerol diglycidyl ether, ethylene glycol, polyethylene glycol, propylene glycol, glycerine, pentaerythritol, ethylenediamine, ethylenecarbonate, propylenecarbonate, polyethylene imine, and glycidyl (meth)acrylate. These cross-linking agents may be used individually, or in combination. These cross-linking agents may be added to the reaction system in a batch manner or in a divisional manner. Among the exemplified compounds, it is preferable to use compounds having a plurality of polymerizable unsaturated groups as the cross-linking agent.

An amount of the cross-linking agent with respect to a total amount of the monomers (excluding the cross-linking agent) is within a range of preferably from 0.01 to 2 mol %, more preferably from 0.03 to 0.2 mol %. If the amount of the cross-linking agent is less than 0.01 mol %, it may be difficult to obtain the water-absorbent resin whose absorption index under a load is not less than 14 g/g by performing a surface cross-linking process described later.

Further, upon initiating the polymerization, it is possible to use a radical polymerization initiator such as potassium persulfate, ammonium persulfate, sodium persulfate, t-butylhydroperoxide, hydrogen peroxide, 2,2'-azobis (2-amidinopropane) dihydrochloride, or a photopolymerization initiator, such as 2-hydroxy-2-methyl-1-phenyl-propane-1-one, or an active energy line and the like, such as an ultraviolet ray and an electron ray. Further, in case of using an oxidative radical polymerization initiator, redox polymerization may be performed using reducer such as sodium sulfite, sodium hydrogen sulfite, ferrous sulfate, and L-ascorbic acid, together. An amount of the polymerization initiators is within a range of preferably from 0.001 to 2 mol %, and more preferably from 0.01 to 0.5 mol %.

Further, it is also preferable to perform such a process that: a blowing agent such as carbonate and an azo compound or inert gas is added to the monomer upon polymerization so that thus obtained water-absorbent resin is made porous, thereby increasing a specific surface area.

Further, for example, a process for producing the water-absorbent resin of the present embodiment includes a series of steps of: preparing a monomer aqueous solution; polymerizing the monomer aqueous solution; refining the polymer into grains; drying the polymer; grinding the polymer; and classifying the polymer.

In case of performing the aqueous solution polymerization, it is general that the aqueous solution is polymerized after preparing a monomer aqueous solution whose concentration ranges from 10 mass % to a saturated concentration, preferably from 20 mass % to 60 mass %. Examples of polymerizing methods include: a method in which the aqueous solution is polymerized with it being stirred in a double-arm kneader as required; a method in which the aqueous solution is polymerized in a container in a casting manner; and a method in which the aqueous solution is (sequentially) polymerized on a driven belt in a static manner.

In order to dry the polymer (hydrous gel) obtained in the polymerization process, it is preferable to refine the hydrous gel into grains having a predetermined particle diameter. It is possible to refine the hydrous gel into grains by polymerizing the hydrous gel while stirring it using a double-arm kneader and the like upon polymerization, or by extruding polymerized gel from a dice using a meat chopper and the like. Further, it is also possible to refine the hydrous gel into grains by using a cutting mill and the like. It is possible to set a particle diameter of the gel refined into grains, depending on a performance etc. of a drier, and the particle diameter is within a range of preferably from 0.1 to 10 mm. If the particle diameter is smaller than 0.1 mm, a property of the obtained water-absorbent resin may be lowered. If the diameter is larger than 10 mm, it may be difficult to dry the obtained water-absorbent resin.

In the step of refining gel into grains, rough gel whose particle diameter is larger than 10 mm and minute gel whose particle diameter is smaller than 0.1 mm can be generated. It is possible to pick up these polymers so as to add them to a monomer aqueous solution or polymerized gel for example.

The gel that had been refined into grains in the step of refining is dried in the step of drying. For example, it is possible to use a hot wind drier, an air stream drier, azeotropic dehydration, a fluidized-bed drier, a drum drier, a micro wave, a far infrared ray, and the like upon drying the gel. A drying temperature is preferably not less than 80° C., and more preferably not less than 120° C., and is more preferably within a range of from 150 to 250° C., and further more preferably from 160 to 220° C.

The water-absorbent resin may be granulated into a predetermined shape, and may be granulated into various shapes such as a spherical shape, a scaly shape, an irregularly crushed shape, and a granular shape. Further, the water-absorbent resin may be shaped as a non-granulated primary particle, or may be shaped as a granulated primary particle.

Generally, the foregoing water-absorbent resin does not satisfy the ranges of the absorption capacity (CRC), the absorption index under a load, and the absorption rate of the present invention. Thus, it is necessary to enhance the cross-link density more in a periphery of a surface of the water-absorbent resin than inside the water-absorbent resin by further using the cross-linking agent. That is, it is possible to obtain the water-absorbent resin which can be used in the present embodiment by cross-linking the periphery of the surface of the water-absorbent resin using the cross-linking agent.

In the present embodiment, it is possible to obtain a water-absorbent resin such that: (i) its surface portion and/or periphery thereof has been subjected to the cross-linking process, and/or (ii) the absorption capacity (CRC) is not less than 25 g/g and not more than 60 g/g and the absorption index under a load is not less than 14 g/g and the absorption rate is not more than 60 seconds, by using the foregoing water-absorbent resin.

That is, the water-absorbent resin according to the present embodiment is obtained by heating preferably the water-absorbent resin obtained by the aforementioned aqueous solution polymerization or reversed phase suspension polymerization, more preferably the water-absorbent resin obtained by the aqueous solution polymerization, that is, the water-absorbent resin obtained by operations such as polymerization and classification performed so that the mass average particle diameter is in a range of from 100 to 600 μm, more preferably from 200 to 500 μm, and an amount of particles whose particle diameter is less than 106 μm is not more than 10 mass %, preferably not more than 5 mass %, more preferably not more than 3 mass %, under presence of the cross-linking agent (hereinbelow referred to as a surface cross-linking agent) which can react with a functional group of the water-absorbent resin.

Note that, the reversed phase suspension polymerization is a polymerization method in which monomer aqueous solution is suspended in hydrophobic organic solvent. For example, this method is recited in U.S. Pat. Nos. 4,093,776, 4,367,323, 4,446,261, 4,683,274, and 5,244,735. The aqueous solution polymerization is a polymerization method in which monomer aqueous solution is polymerized without using dispersal solvent. For example, the method is recited in U.S. Pat. Nos. 4,625,001, 4,873,299, 4,286,082, 4,973,632, 4,985,518, 5,124,416, 5,250,640, 5,264,495, 5,145,906, 5,380,808, and European Patents No. 0811636, No. 0955086, and No. 0922717. Note that, it is possible to apply the monomer and the initiator exemplified in these polymerization methods to the present embodiment.

An example of the surface cross-linking agent is a known cross-linking agent, having a functional group which can react with the functional group of the water-absorbent resin such as an acidic group, which is generally used for the foregoing purpose.

When the functional group of the water-absorbent resin is a carboxyl group, it is possible to exemplify one kind or two or more kinds selected from: polyhydric alcohol compounds, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,4-butanediol, 1,5-pentanediol, 1,6-hexanediol, 1,2-cyclohexanedimethanol, 1,2-cyclohexanediol, trimethylolpropane, diethanolamine, triethanolamine, polyoxypropylene, oxyethylene-oxypropylene block copolymer, pentaerythritol, and sorbitol; epoxy compounds, such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds, such as ethylenediamine, diethylenetriamine, triethylenetetramine, tetraethylenepentamine, pentaethylenehexamine, polyarylamine, and polyethylene-imine; polyisocyanate compounds, such as 2,4-trilene diisocyanate, and hexamethylene diisocyanate; polyoxazoline compounds, such as 1,2-ethylenebisoxazoline; alkylene carbonate compounds, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-dimethyl-1,3-dioxane-2-one, and 1,3-dioxopan-2-one; mono, di, and poly oxazolidine compounds; haloepoxy compounds, such as epichlorohydrin, epibromohydrin, and α-methylepichlorohydrin; polyvalent metal compounds, such as hydroxide and chloride, such as zinc, calcium, magnesium, alminium, iron, and zirconium; silane coupling agents, such as γ-glycidoxypropyltrimetoxysilane, and γ-aminopropyltrietoxysilane; and polyamide-polyamine epihalohydrin resin. Preferably, the cross-linking agent includes at least one kind selected from a polyhydric alcohol compound, a polyamine compound, a polyepoxy compound, and an alkylene carbonate compound.

The amount of the surface cross-linking agent with respect to the water-absorbent resin varies depending on the combination of water-absorbent resin and surface cross-linking agent. However, the amount of the surface cross-linking agent to be used is within a range of preferably from 0.01 mass parts to 5 mass parts, more preferably from 0.01 mass parts to 1 mass part, based on 100 mass parts (weight parts) of the dry water-absorbent resin. By using the above-mentioned surface cross-linking agent, it is possible to improve the cross-link density more in the periphery of the surface of the water-absorbent resin than inside the water-absorbent resin, thereby obtaining the water absorption characteristics required in the resin of the present embodiment. If the amount of the surface cross-linking agent exceeds 10 mass parts, the surface cross-linking agent becomes excessive, causing uneconomical results and drop in the absorption capacity (CRC) upon forming a suitable cross-linking structure in the water-absorbent resin, so that this is not preferable. On the other hand, if the amount of the surface cross-linking agent is less than 0.001 mass parts, it may be difficult to improve the absorption index under a load of the water-absorbent resin.

Upon mixing the water-absorbent resin with the surface cross-linking agent, it is preferable to use water as the solvent. The amount of water varies depending on kinds, particle diameters, and the like of the water-absorbent resin. However, the amount of water to be used is preferably not less than 0 and not more than 20 mass parts, and within a range of more preferably from 0.1 to 10 mass parts, based on 100 parts by mass of the dry water-absorbent resin.

Further, upon mixing the water-absorbent resin with the surface cross-linking agent, a hydrophilic organic solvent may be used as the solvent as required. Examples of the hydrophilic organic solvent include: lower alcohols, such as methyl alcohol, ethyl alcohol, n-propyl alcohol, isopropyl alcohol, n-butyl alcohol, isobutyl alcohol, and t-butyl alcohol; ketones, such as acetone; ethers, such as dioxane, and tetrahydrofuran; amides, such as N,N-dimethylformamide; and sulfoxides, such as dimethyl sulfoxide. The amount of the hydrophilic organic solvent with respect to the water-absorbent resin varies depending on kinds and particle diameters of the water-absorbent resin. However, the amount of hydrophilic organic solvent to be used is preferably not larger than 20 mass parts, more preferably not larger than 10 mass parts, based on 100 parts by mass of the dry water-absorbent resin.

Upon mixing the water-absorbent resin with the surface cross-linking agent, the surface cross-linking agent may be mixed after dispersing the water-absorbent resin in the hydrophilic organic solvent, but the mixing method is not particularly limited. Among various mixing methods, a preferred method is such that: the surface cross-linking agent dissolved in water and/or hydrophilic organic solvent as required is directly mixed to the water-absorbent resin in a spraying or dropping manner. Further, when mixing the cross-linking agent using water, fine-grain powder which is not soluble in water, a surface active agent, and the like may coexist.

A mixer for use in mixing the water-absorbent resin and the surface cross-linking agent preferably has a great mixing power so as to mix them evenly and surely. Preferred examples of the mixer are a cylindrical mixer, double-wall conical mixer, V-shaped mixer, ribbon blender, screw mixer, fluid oven rotary desk mixer, airborne mixer, double-arm kneader, internal mixer, crush-type kneader, rotary mixer, and screw extruder.

In order to obtain the water-absorbent resin used in the present embodiment, that is, in order to obtain a water-absorbent resin having the following characteristics: (i) its surface and/or a periphery thereof has been treated by a cross-linking agent which is reactive with a functional group of the water-absorbent resin, and/or (ii) the absorption capacity is not less than 25 g/g and not more than 60 g/g, and the absorption index under a load is not less than 14 g/g, and the absorption rate is not less than 60 seconds, it is preferable to perform a heating treatment after mixing the water-absorbent resin and the cross-linking agent.

The treatment temperature varies depending on the surface cross-linking agent. However, the heating treatment is performed so that a temperature of the mixture obtained by mixing the water-absorbent resin with the surface cross-linking agent is preferably not less than 40° C. and not more than 250° C., more preferably not less than 90° C. and not more than 210° C. If the treatment temperature is less than 40° C., a cross-linking structure is not evenly formed, so that it may be impossible to obtain the water-absorbent resin whose absorption index under a load covers the range of the present embodiment. If the treatment temperature exceeds 250° C., quality of the water-absorbent resin is deteriorated, so that characteristics of the water-absorbent resin may be deteriorated.

The heating treatment can be performed using an ordinary drier or heating oven.

Examples of the heating oven includes a channel mixing drier, a rotary drier, a desk drier, a fluidized-bed drier, a pneumatic conveyor drier, and an infrared drier.

In order to obtain the water-absorbent resin which can be used in the present embodiment, it is preferable to control the cross-linking agent, a mixing method, a heating temperature, and a treatment time so that the absorption index under a load is not less than 14 g/g.

It is possible to obtain the water-absorbent resin of the present embodiment by adding a semi-fermented tea extract and/or a fermented tea extract to such water-absorbent resin that (i) its surface and/or a periphery thereof is preferably treated by the cross-linking agent, and or such water-absorbent resin that: (ii) the absorption capacity (CRC) is not less than 25 g/g and not more than 60 g/g, preferably not less than 27 g/g, more preferably not less than 29 g/g, further more preferably not less than 31 g/g, and the absorption index under a load is not less than 14 g/g, preferably not less than 16 g/g, more preferably not less than 18 g/g, further more preferably not less than 20 g/g, and the absorption rate is not more than 60 seconds, preferably not more than 55 seconds, more preferably not more than 50 seconds.

The semi-fermented tea extract and/or the fermented tea extract that can be used in the present embodiment is a kind of a plant extract, and is preferably an extract of semi-fermented tea manufactured from theaceous indeciduous shrubbery and leaves thereof and/or an extract of fermented tea manufactured from theaceous indeciduous shrubbery and leaves thereof. The semi-fermented tea extract and/or the fermented tea extract is obtained by extracting the semi-fermented tea and/or the fermented tea with an extract agent made of organic solvent, aqueous solvent, or mixture solvent of the organic solvent and the aqueous solvent. In the present invention, the extract means an extracted essence (element), and an extract agent such as an extract solvent is not included in the extract.

Generally, the theaceous tea is roughly categorized into three kinds: non-fermented tea (green tea), semi-fermented tea (Chinese tea such as oolong tea), and fermented tea (red tea), due to differences in processing, and this categorization is based on how oxidative enzyme contained in the tea leaf reacts. The green tea is such that picked leaves were immediately fumigated or roasted at high temperature so as to stop its oxidative enzyme from working, and the green tea is generally referred to as non-fermented tea. The oolong tea is such that picked leaves were heated after being slightly oxidized so as to stop the reaction, and the oolong tea is generally referred to as semi-fermented tea. The red tea is such that picked leaves were ground up after being slightly dried for oxidization, and the red tea is generally referred to as fermented tea. Among these kinds of tea, the semi-fermented tea extract and/or the fermented tea extract has the peculiarly gentle fragrance, and is preferably used in the present embodiment as long as it exhibits the superior deodorant performance.

Some absorbing products, such as a diaper, using general water-absorbent resin containing such semi-fermented tea extract and/or fermented tea extract do not sufficiently provide the deodorant performance to the whole diaper, so that the absorbing products may make the user uncomfortable. The water-absorbent composition of the present embodiment solves the foregoing problem by specifying the property of the water-absorbent resin that has not been mixed with the semi-fermented tea extract and/or the fermented tea extract, so that it is possible to provide the superior deodorant performance and the superior absorbent characteristic to the absorbing product. Thus, it is preferably used in the absorbing product.

The process for producing the semi-fermented tea extract and the fermented tea extract is not particularly limited, but it is possible to obtain the semi-fermented tea extract and/or the fermented tea extract by causing an extract agent constituted of organic solvent and aqueous solvent or mixture solvent of the organic solvent and the aqueous solvent to perform extraction with respect to leaves and stems of the semi-fermented tea and/or the fermented tea upon heating from an ordinary temperature.

The amount of the used semi-fermented tea extract and/or fermented tea extract (the amount of the added semi-fermented tea extract and/or fermented tea extract) varies depending on what kind of deodorant performance is required. However, the amount is in a range of preferably from 0.001 mass parts to 20 mass parts, more preferably from 0.001 mass parts to 10 mass parts, further more preferably from 0.01 mass parts to 5 mass parts with respect to 100 mass parts of the dry water-absorbent resin.

Examples of a process for adding the semi-fermented tea extract and/or the fermented tea extract are as follows: the semi-fermented tea extract and/or the fermented tea extract is sprayed or dropped directly to the water-absorbent resin so that a desired amount of the semi-fermented tea extract and/or the fermented tea extract is added to the water-absorbent resin; and the semi-fermented tea extract and/or the fermented tea extract is sprayed or dropped to the water-absorbent resin after dissolving or dispersing the extract in aqueous solution or various kinds of organic solvent. Note that, it is also possible to use a process in which the semi-fermented tea extract and/or the fermented tea extract is added upon polymerizing the water-absorbent resin or a process in which the semi-fermented tea extract and/or the fermented tea extract is added to the polymerized gel, but it is necessary to perform subsequent steps so that the absorption capacity (CRC), the absorption index under a load, and the absorption rate of the present embodiment can be obtained.

Further, another example of the process for adding the semi-fermented tea extract and/or the fermented tea extract is as follows: various kinds of inorganic or organic powder containing the semi-fermented tea extract and/or the fermented tea extract in advance is directly mixed with the water-absorbent resin. Note that, it is also possible to use a process in which the powder is added upon polymerizing the water-absorbent resin or a process in which the powder is added to the polymerized gel, but it is necessary to perform subsequent steps so that the absorption capacity (CRC), the absorption index under a load, and the absorption rate of the present embodiment can be obtained.

Examples of inorganic or organic powder preferably used for adding the semi-fermented tea extract and/or the fermented tea extract of the present embodiment include: inorganic powder, such as silicon dioxide, titanium dioxide, aluminium oxide, magnesium oxide, zinc oxide, clay, talc, calcium phosphate, barium phosphate, silicic acid or salt thereof, clayey materials, diatom earth, silica gel, zeolite, bentonite, kaolin, hydroxyapatite, hydrotalcite, vermiculite, perlite, isolite, activated clay, quartz sand, quartz rock, strontium ore, fluorite, and bauxite; polyethylene, polypropylene, polyvinylchloride, polystyrene, nylon, melanin resin, polymethylmethacrylate, starch, dextrin, cyclodextrin, and the like. Among them, one kind or two or more kinds can be used. Starch and dextrin are preferably used.

Among the organic or inorganic powder, a particle whose particle diameter is minute is specifically preferable. It is possible to use a particle whose particle diameter is not more than 100 µm, preferably not more than 50 µm, more preferably not more than 10 µm. Note that, the lower limit of the particle diameter of the inorganic and organic powder is preferably not less than 1 nm in view of workability and a mixing property. Further, among the organic or inorganic powder, powder slightly colored or powder little colored is preferably used since it is possible to improve whiteness degree of the water-absorbent resin which is a final product.

When mixing the semi-fermented tea extract and/or the fermented tea extract with the inorganic or organic powder, the semi-fermented tea extract and/or the fermented tea extract may be individually sprayed or dropped directly to the inorganic or organic powder, but the extract may be sprayed or dropped after dissolving the extract in aqueous solution or various kinds of organic solvent.

It is preferable to set the amount of the semi-fermented tea extract and/or the fermented tea extract is within a range of from 0.001 to 20 mass parts with respect to 100 mass parts of the dry water-absorbent resin as described above, and it is general that the amount of the semi-fermented tea extract and/or the fermented tea extract is within a range of generally from 1 to 500 mass parts with respect to 100 mass parts of the inorganic or the organic powder, preferably from 5 to 50 mass parts of the inorganic or the organic powder. If the amount of the semi-fermented tea extract and the fermented tea extract exceeds 50 mass parts, the mixture tends to be slurry. Thus, at a time when the extract is mixed with the water-absorbent resin, reaction or absorption is initiated, so that it may be difficult to keep the stable deodorant characteristic with a passage of time. Further, if the amount of the semi-fermented tea extract and/or the fermented tea extract is less than 1 mass part, the amount of the inorganic or organic powder containing the semi-fermented tea extract and/or the fermented tea extract is large with respect to the water-absorbent resin to be reformed, so that the obtained water-absorbent resin tends to be inferior in the absorbent characteristic.

In the present embodiment, when mixing the water-absorbent resin with the semi-fermented tea extract and/or the fermented tea extract, the most appropriate amounts of added water, moisture vapor, or aqueous solution constituted of water and hydrophilic organic solvent and the like vary depending on kinds or particle sizes of the water-absorbent resin. However, the amount of water is generally not more than 10 mass parts, preferably within a range of from 1 to 5 mass parts with respect to 100 mass parts of the dry water-absorbent resin. Further, likewise, the amount of the used hydrophilic organic solvent is generally not more than 10 mass part, preferably within a range of from 0.1 to 5 mass parts.

In the present embodiment, an ordinary apparatus is used as an apparatus used in mixing the water-absorbent resin with the semi-fermented tea extract and/or the fermented tea extract, and examples of the apparatus include a cylindrical mixer, screw mixer, screw extruder, turbulizer, nauta mixer, V-shaped mixer, ribbon blender, double-arm kneader, fluid mixer, pneumatic conveyor mixer, rotating disc mixer, roll mixer, and convolution mixer. It does not matter whether the mixing speed is high or low.

Various kinds of inorganic powder may be further added to the water-absorbent resin and/or the water-absorbent composition. Examples of the inorganic powder specifically include: metal oxide such as silicon dioxide and titanium oxide; silicate (salt) such as natural zeolite and synthetic zeolite; and kaolin, talc, clay, and bentonite. Among them, silicon dioxide and silicate (salt) are preferable, and silicon dioxide and silicate (salt) each of which has an average particle diameter of not more than 200 µm based on measurement by Coulter Counter Method are more preferable. The amount of the inorganic powder varies depending on how the water-absorbent resin and/or water-absorbent composition is combined with the inorganic powder. However, the amount of the inorganic powder preferably ranges from 0.001 mass parts to 10 mass parts, more preferably from 0.01 mass parts to 5 mass parts, still more preferably from 0.01 to 3 mass parts, further more preferably from 0.01 to 1 mass parts, with respect to 100 mass parts of the water-absorbent resin and/or the water-absorbent composition. The process for mixing the water-absorbent resin and/or the water-absorbent composition with the inorganic powder is not particularly limited, and it is possible to use, for example, a dry blending process, wet blending process, and the like, but the dry blending process is more preferable.

The water-absorbent composition obtained by the foregoing producing methods includes: a semi-fermented tea extract and/or a fermented tea extract; a water-absorbent resin whose surface has been treated; and/or a water-absorbent resin whose absorption capacity (CRC) is not less than 25 g/g and not more than 60 g/g and absorption index under a load is not less than 14 g/g and absorption rate is not more than 60 seconds (that is, more than 0 and not more than 60 seconds).

By making selection of the water-absorbent resin, it is possible to obtain a water-absorbent composition whose deodorant effect is high in practical use as the water-absorbent composition of the present embodiment.

The water-absorbent composition of the present embodiment is preferably such that the absorption capacity (CRC) is not less than 25 g/g and not more than 60 g/g and the absorption index is not less than 14 g/g and the absorption rate is not more than 60 seconds.

The absorption capacity (CRC) is more preferably not less than 27 g/g, still more preferably not less than 29 g/g, particularly preferably not less than 31 g/g. If the absorption capacity (CRC) is less than 25 g/g, the absorption amount is not sufficient, so that this is not preferable. If the absorption capacity (CRC) is more than 60 g/g, gel strength is not sufficient, so that a gel blocking phenomenon tends to occur. Thus, this is not preferable.

The absorption index under a load is a new parameter for measuring a force by which the water-absorbent resin absorbs liquid from the paper, and is represented by a value obtained by adding (a) a value measured in three minutes after initiation of absorption to (b) a value measured in 60 minutes after initiation of absorption. If thus obtained value is large, the force by which the water-absorbent composition absorbs the liquid therearound is strong. Thus, the water-absorbent composition absorbs excreted liquid such as stinking urine and menstrual blood, so that the water-absorbent composition enhances the deodorant effect of the semi-fermented tea extract and the fermented tea extract. Further, the action is superior not only in the deodorant effect of the water-absorbent composition but also in a deodorant effect of the absorbing product. The absorption index under a load is more preferably not less than 16 g/g, still more preferably not less than 18 g/g, and particularly preferably not less than 20 g/g. As the upper limit of the absorption index under a load is higher, it becomes more preferable, but not more than 40 g/g is preferable in terms of a performance balance with the absorption capacity (CRC).

The absorption rate is more preferably not more than 55 seconds, still more preferably 50 seconds. If the absorption rate exceeds 60 seconds, the absorption is delayed, and the deodorant effect is deteriorated, so that this is not preferable.

Further, the absorption characteristics represented by the absorption capacity (CRC), the absorption index under a load, and the absorption rate can realize not only the superior deodorant effect but also small leakage, small returning amount, prevention of hip-skin fit, and dry touch, in practical use of the water-absorbing product.

As to the water-absorbent composition of the present embodiment, the mass average particle diameter is within a range of preferably from 100 µm to 600 µm, more preferably from 200 µm to 500 µm, and a ratio of particles whose mass average particle diameter is less than 106 µm is preferably not more than 10 mass %, more preferably not more than 5 mass %, and still more preferably not more than 3 mass %.

Further, as described above, the water-absorbent resin according to the present embodiment is a particulate water-absorbent resin (particulate water-absorbent resin composition) made mainly of water-absorbent resin (A), having a cross-linking structure obtained by polymerizing an unsaturated monomer containing acid groups, and it is preferable that the water-absorbent composition has a specific neutralization rate and a specific particle diameter. Note that, the water-absorbent composition is described in Embodiment 2 as well as a case where a plant extract other than the semi-fermented tea extract and/or the fermented tea extract is used as the plant component (B).

It is preferable to use the water-absorbent composition of the present embodiment as a sanitary material. Further, it is possible to use the water-absorbent composition of the present embodiment also as a deodorant. The water-absorbent resin included in the water-absorbent composition is superior in the absorbing ability (neutralizing ability) with respect to an amine element or an ammonia element. Thus, a synergy effect of (a) the deodorant effect brought about by the water-absorbent resin and (b) the deodorant effect brought about by the plant component (B) such as the semi-fermented tea extract and/or the fermented tea extract causes the water-absorbent composition to exhibit the superior deodorant effect.

The absorbent of the present embodiment is an absorbent material including the water-absorbent composition of the present embodiment. The absorbent can be obtained as follows: for example, the water-absorbent composition is coagulated by adhesive or by blending with fiber materials such as a hydrophilic fiber, or the water-absorbent composition is provided (sandwiched) between the fiber materials, and is then molded. It is possible to preferably use the absorbent as an absorbent layer of an absorbing product such as a sanitary material.

The absorbent of the present embodiment may arranged so that the water-absorbent composition is sandwiched between fibers other than the hydrophilic fibers such as tissue paper, or may be arranged so that the water-absorbent composition is merely coagulated by the adhesive and the like. That is, the absorbent of the present embodiment may be arranged so that the core concentration, i.e., the amount of the included water-absorbent composition with respect to a total mass of the water-absorbent composition and the hydrophilic fiber is 100 mass %. However, the absorbent includes the hydrophilic fiber, so that it is possible to stably and easily obtain the absorbent which is superior in the absorbent characteristic and can be easily provided in the absorbing product such as a diaper.

When the absorbent includes the hydrophilic fiber, the upper limit of the amount (core concentration) of the added water-absorbent composition with respect to a total mass of the water-absorbent composition and the hydrophilic fiber is not limited. The core concentration can be arbitrarily set within a range of less than 100 mass %, but is set preferably within a range of from 10 to 90 mass %, more preferably from 20 to 90 mass %, further preferably from 25 to 80 mass %. When the core concentration is less than 10 mass %, the amount of the water-absorbent composition is little, so that the sufficient deodorant effect sometimes is not provided to a whole diaper. Thus, this is not preferable. Further, when the core concentration exceeds 90 mass % (that is, the amount of the included hydrophilic fiber with respect to the total mass of the water-absorbent composition and the hydrophilic fiber is less than 10 mass %), there is possibility that the use of the hydrophilic fiber may not provide the sufficient effect.

Note that, when the absorbent includes the fiber material such as the hydrophilic fiber, the semi-fermented tea extract and/or fermented tea extract may be included in the water-absorbent composition by mixing the extract with the water-absorbent composition, or may be included by adding the extract to the fiber material such as the hydrophilic fiber, or may be included by adding the extract after blending the water-absorbent resin to the fiber material such as the hydrophilic fiber. That is, in the absorbent, the semi-fermented tea extract and/or the fermented tea extract may be included in the water-absorbent composition, or may be included (in the fiber material such as the hydrophilic fiber) separately from the water-absorbent composition.

Further, the water-absorbing product of the present embodiment includes: an absorbent (absorbent layer) containing the water-absorbent composition of the present invention; a surface sheet having liquid permeability; and a back sheet having liquid impermeability.

The water-absorbing product of the present embodiment is preferably such that a mass ratio of the water-absorbent composition contained in the absorbent layer is not less than 0.1, preferably ranges from 0.2 to 0.9, more preferably ranges from 0.25 to 0.8.

As to the water-absorbing product of the present embodiment, if the mass ratio of the water-absorbent composition contained in the absorbent layer is less than 0.1, the amount of the water-absorbent composition is little, so that sufficient deodorant effect may not be provided to a whole diaper. Thus, this is not preferable.

The water-absorbent resin constituting the water-absorbent composition contained in the absorbent layer of the absorbing product of the present embodiment is made mainly of cross-linked polyacrylic acid (salt).

The water-absorbent composition contained in the absorbent layer of the absorbing product of the present embodiment is preferably such that the absorption capacity (CRC) is not less than 25 g/g and not more than 60 g/g and the absorption index under a load is not less than 14 g/g and the absorption rate is not more than 60 seconds. The absorption capacity (CRC) is more preferably not less than 27 g/g, still more preferably 29 g/g, and particularly preferably not less than 31 g/g. The absorption index under a load is more preferably not less than 16 g/g, still more preferably not less than 18 g/g, and particularly preferably not less than 20 g/g. The absorption rate is more preferably not less than 55 seconds, and still more preferably not less than 50 seconds.

An example of the method for producing the water-absorbing product is as follows: fiber base materials and the water-absorbent composition are blended or the water-absorbent composition is sandwiched by the fiber base materials so as to form the absorbent layer (absorbent core), and the absorbent core is sandwiched by a base material having the liquid permeability (surface sheet) and a base material having the liquid impermeability (back sheet), and an elastic member, a diffusing layer, an adhesive tape, and the like are provided, thereby obtaining an absorbing product, particularly an adult diaper or a sanitary napkin. Such absorbent core is formed in a compression manner so that the density is within a range of from 0.06 to 0.50 g/cm$^3$ and the capacity of scale is within a range of from 0.01 to 0.20 g/cm$^2$ for example. Note that, examples of the fiber base material include: a hydrophilic fiber such as crushed wood pulp; cotton linter and cross-linking cellulose fiber; rayon, cotton; wool; acetate; and vinylon. It is preferable to perform an air-laid process with respect to them.

As the hydrophilic fiber, wood pulp that has been crushed by a machine, chemical pulp, kraft pulp, arboreous cotton, rayon, cotton, wool, acetate, vinylon, polyolefin fiber, and polyester fiber are preferably used. A single fiber may be used, or two or more fibers combined in a stacking manner or sheathing manner may be used. Among the fibers, a fiber whose surface is hydrophobic is subjected to a hydrophilic process.

In this way, the water-absorbent composition of the present embodiment can provide the superior deodorant function to the absorbing product and exhibits the superior deodorant property and the superior absorbent characteristic for a long time. Examples of such absorbing product specifically include sanitary materials such as an adult diaper being developed recently, a baby diaper, a sanitary napkin, a so-called incontinence pad, but the use is not limited to these materials. The water-absorbent composition which exists in the absorbing product has the superior deodorant characteristic, and returns little liquid, and realizes good dry touch, so that it is possible to largely reduce the load of the wearer and care givers.

Embodiment 2

Next, the following description will discuss a particulate water-absorbent composition (particulate water-absorbent resin composition) having three characteristics: (1) a specific neutralization rate, (2) a specific particle diameter, and (3) a specific plant extract.

First, a water-absorbent resin used in the present embodiment is described.

(I) Water-Absorbent Resin

The water-absorbent resin used in the present embodiment is a water-swelling and water-insoluble cross-linked polymer which can form hydrogel. For example, the water-swelling means to essentially absorb a large amount of water five times as large as, preferably 50 to 1000 times as large as a mass of the dry water-absorbent resin in ion exchange water, and "water-insoluble" means that: concentration of the uncross-linked water-soluble element (water-soluble macromolecule) contained in the water-absorbent resin is preferably not more than 50 mass %, more preferably not more than 25 mass %, still more preferably not more than 20 mass %, further still more preferably not more than 15 mass %, particularly preferably not more than 10 mass %. Note that, a measuring method thereof will be defined in Examples.

As the water-absorbent resin of the present embodiment, a water-absorbent resin (A), having a cross-linking structure obtained by polymerizing unsaturated monomer containing acid groups, is essentially used in terms of the deodorant effect and the absorbent characteristic. Note that, also a monomer, such as acrylnitryl, which becomes acid group as the acid group monomer due to hydrolysis after polymerization is used as the acid group monomer in the present embodiment, but an acid group monomer which contains acid group upon polymerization is preferably used.

As in the water-absorbent resin exemplified in Embodiment 1, examples of the water-absorbent resin include one kind of or mixture of partially neutralized and cross-linked polyacrylic acid, hydrolyzed starch-acrylonitrile graft polymer, saponified vinyl acetate-acrylic ester copolymer, hydrolyzed acrylonitrile copolymer or acrylamide copolymer, or cross-linked acrylonitrile copolymer or acrylamide copolymer, carboxylic cross-linked and denaturated polyvinyl alcohol, cross-linked isobutylene-maleic anhydride copolymer. It is preferable to use partially neutralized and cross-linked polyacrylic acid obtained by polymerizing and cross-linking monomer mainly made of acrylic acid and/or salt (neutralized acrylic acid) thereof.

When acrylic acid and/or salt thereof is a main element, other monomer may be used. The monomer used together is exemplified in U.S. Patents and European Patent described in Embodiment 1. Note that, as the copolymerization component, it is possible to use water-soluble or hydrophobic unsaturated monomers such as methacrylic acid, maleic acid, maleic anhydride, fumaric acid, crotonic acid, itaconic acid, vinyl sulfonic acid, 2-(meth)acrylamido-2-methylpropane sulfonic acid, (meth)acryloxy alkane sulfonic acid and alkali metallic salt thereof, ammonium salt, N-vinyl-2-pyrrolidone, N-vinyl acetamide, (meth)acrylamide, N-isopropyl (meth)acrylamide, N,N-dimethyl (meth)acrylamide, 2-hydroxyethyl (meth)acrylate, methoxypolyethylene glycol (meth)acrylate, polyethylene glycol (meth)acrylate, isobutylene, and lauryl (meth)acrylate.

In case of using a monomer other than acrylic acid (salt) in the present embodiment, a ratio of the monomer other than acrylic acid (salt) is preferably not more than 30 mol %, more preferably not more than 10 mol %, with respect to a total amount of acrylic acid and salt thereof used as main elements. By using a monomer other than acrylic acid (salt) together with acrylic acid (salt), it is possible to further improve the absorbent characteristic of the final water-absorbent resin (composition), and it is possible to obtain the water-absorbent (composition) at further lower cost.

It is necessary for the water-absorbent resin to have a cross-linking structure. Then, the cross-linking structure may be formed in a self cross-linking manner without using a cross-linking agent, but the cross-linking structure is more preferably formed by copolymerizing or reacting a cross-linking agent (internal cross-linking agent of the water-absorbent resin) having two or more polymerizable unsaturated groups or two or more reactive groups in a single molecule.

As a specific example of the internal cross-linking agent, it is possible to use the cross-linking agents exemplified in Embodiment 1 as the internal cross-linking agent. A single cross-linking agent of these cross-linking agents may be used, or two or more cross-linking agents may be used in combination as required. Further, the cross-linking agents may be added to the reaction system in a batch manner or a divisional manner as in Embodiment 1. Also in the present embodiment, in case of using one kind or two or more kinds of internal cross-linking agents, it is preferable to essentially use a compound having two or more polymerizable unsaturated groups upon polymerization in consideration for the absorbent characteristic and the like of the water-absorbent resin and the water-absorbent composition that are finally obtained.

The amount of the internal cross-linking agent preferably ranges from 0.001 to 2 mol %, more preferably from 0.005 to 0.5 mol %, still more preferably ranges from 0.01 to 0.2 mol %, particularly preferably ranges from 0.03 to 0.15 mol %, with respect to the amount of the monomer (excluding the cross-linking agent). In case where the amount of the internal cross-linking agent is less than 0.001 mol %, and in case where the amount is more than 2 mol %, sufficient absorbent characteristic may not be obtained.

In case of introducing the cross-linking structure into the polymer by using the internal cross-linking agent, the internal cross-linking agent is added to the reaction system before or upon or after the polymerization of the monomer, or after the neutralization of the monomer.

When polymerizing the aforementioned monomer so as to obtain the water-absorbent resin used in the present embodiment, it is possible to perform bulk polymerization or precipitable polymerization, but it is preferable to perform aqueous solution polymerization or reversed phase suspension polymerization, in which the monomer is contained in aqueous solution, in terms of performance, easiness to control the polymerization, and the absorbent characteristic of the swelling gel.

The concentration of the monomer in aqueous solution in case where the monomer is contained in the aqueous solution (hereinbelow referred to as monomer aqueous solution) is determined depending on a temperature and the monomer of the aqueous solution, and is not particularly limited. However, the concentration is within a range of preferably from 10 to 70 mass %, more preferably from 20 to 60 mass %. Further, when performing the aqueous solution polymerization, solvent other than water may be used together as required, and what kind of solvent used together is not particularly limited.

Note that, the reversed phase suspension polymerization is a polymerization method in which monomer aqueous solution is suspended in hydrophobic organic solvent as described in Embodiment 1. It is possible to apply the monomer and the initiator, exemplified in the polymerization methods recited in U.S. Patents and European Patents cited in Embodiment 1 concerning the reversed phase suspension polymerization, to the present embodiment.

Upon initiating the polymerization, it is possible to use a radical polymerization initiator or a photopolymerization initiator described in Embodiment 1. The amount of the polymerization initiator preferably ranges from 0.001 to 2 mole %, and more preferably ranges from 0.01 to 0.1 mole % (with respect to the whole amount of monomers).

After the polymerization, the resultant is hydrophilic gelatinous cross-linking polymer in an ordinary state, and is dried as required, and is ordinarily ground before and/or after being dried, so as to be used as the water-absorbent resin. Further, the drying treatment is performed at a temperature ordinarily ranges from 60° C. to 250° C., preferably ranges from 100° C. to 220° C., more preferably ranges from 120° C. to 200° C. A drying time is determined depending on a surface area and a moisture content of the polymer, and depending on what kind of drier is used, so as to realize an aimed moisture content.

The moisture content (amount of water contained in the water-absorbent resin or the water-absorbent composition: measured in terms of drying loss under a condition where the water-absorbent resin is dried at 180° C. for three hours) of the water-absorbent resin (water-absorbent composition) which can be used in the present embodiment is not particularly limited, but the obtained water-absorbent composition is powder whose property is fluid at a room temperature, so that the water-absorbent composition is preferably powder whose amount more preferably ranges from 0.2 to 30 mass %, still more preferably ranges from 0.3 to 15 mass %, particularly preferably ranges from 0.5 to 10 mass %. A preferable particle diameter of the water-absorbent resin (water-absorbent composition) is described later.

A particle shape of thus obtained water-absorbent resin or the water-absorbent composition is not limited to a spherical shape, a crushed shape, an amorphous shape, and the like, but the amorphous-shaped water-absorbent resin obtained after performing the crushing step is preferably used. Further, its bulk density (prescribed in JIS K-3362) is within a range of preferably from 0.40 to 0.80 g/ml, more preferably from 0.50 to 0.75 g/ml, still more preferably from 0.60 to 0.73 g/ml, in terms of the superior property of the water-absorbent composition.

The water-absorbent resin used in the water-absorbent composition of the present embodiment may be obtained by the aforementioned cross-linking polymerization and the drying treatment, but it is more preferable to further cross-link (secondary cross-link) a surface thereof.

There are various kinds of cross-linking agent for performing the surface cross-linking. In terms of the property, it is general to use polyalcoholic compound, epoxy compound, polyamine compound or condensate of polyamine compound and haloepoxy compound, oxazoline compound, mono, di, or poly oxazolidinon compound, polyvalent metal salt, alkylene carbonate compound, and the like.

The surface cross-linking agent used in the present embodiment are specifically exemplified in U.S. Pat. Nos. 6,228,930, 6,071,976, and 6,254,990. Examples of the surface cross-linking agent include: polyhydric alcohol compounds, such as mono, di, tri, tetra, or polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, 1,2-cyclohexanedimethanol; epoxy compounds, such as ethylene glycol diglycidyl ether and glycidol; polyamine compounds, such as ethylenediamine, diethylenetriamine, triethylenetetramine, tetraethylenepentamine, pentaethylenehexamine, polyethylene-imine, polyamidopolyamine; haloepoxy compounds, such as epichlorohydrin, epibromohydrin, and α-methylepichlorohydrin; condensate of the polyamine compound and the haloepoxy compound, oxazolidinon compounds such as 2-oxazolidinon, alkylene carbonate compounds such as ethylene carbonate. However, the surface cross-linking agent is not particularly limited to them. It is preferable to use at least polyalcohol among these cross-linking agents so as to maximize the effect of the present embodiment, so that polyalcohol containing 2 to 10 carbon atoms, preferably 3 to 8 carbon atoms, is used.

The amount of the surface cross-linking agent varies depending on used compounds and combinations thereof. However, the amount is within a range of preferably from 0.001 mass parts to 10 mass parts, more preferably from 0.01 mass parts to 5 mass parts, with respect to 100 mass parts of the water-absorbent resin.

In the present embodiment, it is preferable to use water for the surface cross-linking. In this case, the amount of the water varies depending on the moisture content of the used water-absorbent resin. However, it is general that the amount ranges from 0.5 to 20 mass parts, preferably ranges from 0.5 to 10 mass parts, with respect to 100 mass parts of the water-absorbent resin. Further, in the present embodiment, hydrophilic organic solvent may be used as well as water. The amount of the hydrophilic organic solvent ranges from 0 to 10 mass parts, preferably ranges from 0 to 3 mass parts, with respect to the amount of the water-absorbent resin. At this time, the amount of the hydrophilic organic solvent is within a range of from 0 to 10 mass parts, preferably from 0 to 5 mass parts, more preferably from 0 to 3 mass parts.

Further, among various kinds of mixing methods, it is preferable to employ the following method in the present embodiment: after mixing water and/or hydrophilic organic solvent as required in advance, the aqueous solution is sprayed or dropped to the water-absorbent resin so as to be mixed. It is more preferable to spray the aqueous solution. A size of a sprayed droplet is preferably not more than 300 μm, more preferably not more than 200 μm. Further, upon mixing, water-insoluble-fine-particle powder and surface-active agent may be made to coexist as long as the effect of the present invention is not prevented.

The water-absorbent resin in which the cross-linking agent has been mixed is preferably heated. The heating treatment is performed so that: a temperature of a mixture obtained by mixing the water-absorbent resin with the cross-linking agent is within a range preferably from 100 to 250° C., more preferably from 150 to 250° C. A heating time is within a range of preferably from one minute to two hours. Preferable examples of a combination of the temperature and the time are such that: the heating treatment is preferably performed at 180° C. for 0.1 to 1.5 hours, or at 200° C. for 0.1 to 1 hour.

The water-absorbent resin obtained by performing the surface cross-linking as required is adjusted to a specific particle size so as to achieve the deodorant effect of the present invention. It is preferable that the amount of particles whose particle diameter is less than 850 μm and not less than 150 μm is not less than 90 mass % with respect to the whole and the amount of particles whose particle diameter is not less than 300 μm is 60 mass % with respect to the whole. It is more preferable that the amount of the particles whose particle diameter is less than 850 μm and not less than 150 μm is not less than 95 mass %, further more preferably not less than 98 mass %. The amount of the particles whose particle diameter is not less than 300 μm is more preferably not less than 65 mass %, still more preferably not less than 70 mass %, particularly preferably not less than 75 mass %. Further, a mass average particle diameter of the water-absorbent resin preferably ranges from 200 to 700 μm, still more preferably ranges from 300 to 600 μm, further still more preferably ranges from 400 to 500 μm. The foregoing particle diameter is applied also to a water-absorbent composition described later, and the particle diameter of the water-absorbent resin or the water-absorbent composition may be adjusted by granulation and the like.

The water-absorbent composition of the present embodiment can be obtained by adding a plant component (B) containing at least one kind of compound, preferably two or more kinds of compounds, more preferably three or more kinds of compounds, selected from polyphenol, flavones, and caffeine, to the water-absorbent resin (A) obtained by the aforementioned manner.

(II) Plant Component (B)

The plant component (B) that can be used in the present embodiment is a plant extract containing at least one kind of compound, preferably two or more kinds of compounds, more preferably three or more kinds of compounds, selected from polyphenol, flavones, and caffeine so that its amount exceeds 0 and is not more than 100 mass %. It is preferable that the compound is at least one kind of compound selected from tannin, tannic acid, gallnut, nutgall, and gallic acid.

Examples of a plant containing the plant component (B) that can be used in the present embodiment include: theaceous plant such as camellia, Eurya japonica, and Ternstroemia gymnanthera; a rubiaceous plant such as coffee; and gramineous plant such as rice, bamboo grass, bamboo, Indian corn, and wheat.

The amount of the plant component (B) varies depending on the aimed deodorant function. However, the amount of added plant component (B) is within a range of preferably from 0.001 to 10 mass parts, more preferably from 0.01 to 5 mass parts, with respect to 100 mass parts of the dry water-absorbent resin. If the amount is less than 0.001 mass parts, it is impossible to obtain sufficient effect. If the amount is not less than 10 mass parts, it is impossible to obtain effect corresponding to the amount of added plant component (B).

The plant component (B) that can be used in the present embodiment contains the aforementioned compound, and examples thereof include: a plant extract (ethereal oil); a plant itself (plant powder); a plant residue and an extract residue which are by-products generated upon production in a plant processing industry or a food processing industry, and the like. Further, since the plant component (B) is extracted almost from a natural material, an antibacterial agent, a bactericide, a sterilizer, a bacteria eradicator, a bacteriostatic agent, a disinfectant, a bactericide, a preservative, and the like may be included in the plant component (B) in advance.

Further, in case where the plant component (B) itself is powder, and/or in case where the plant component (B) is powder which has an extract (essential oil) containing the plant component (B) extracted from a plant, its particle diameter is within a range of generally from 0.001 to 1000 μm, preferably from 1 to 600 μm, and a mass average particle diameter is not more than 500 μm, more preferably not more than 300 μm. If the mass average particle diameter is more than 500 μm, when the water-absorbent resin comes into contact with urine, an active element contained in the plant component (B) insufficiently acts, so that it may be impossible to realize the stable deodorant function. Thus, this is not preferable. Further, if the mass average particle diameter of the powder containing the plant component (B) is smaller than the mass average particle diameter of the water-absorbent resin, it is possible to realize the superior deodorant performance and stability, so that this is preferable.

The plant component (B) that can be used in the present embodiment is preferably liquid and/or aqueous solution at an ordinary temperature so as to be added to the water-absorbent resin as described later.

(III) Water-Absorbent Composition

The water-absorbent composition used in the present embodiment includes the plant component (B) used in the present embodiment and the water-absorbent resin used in the present embodiment, and the water-absorbent composition is characterized in that the amount of particles whose particle diameter is less than 850 μm and not less than 150 μm is 90 mass % with respect to the whole and the amount of particles whose particle diameter is not less than 300 μm is 60 mass % with respect to the whole.

As long as the water-absorbent composition includes the plant component (B) and the water-absorbent resin, a producing process thereof is not particularly limited. For example, it is possible to employ such process that the plant component (B) is added to the water-absorbent resin. Examples of the adding process include: a process in which solution containing the plant component (B) is sprayed or dropped so that a desired amount of the solution is added to the water-absorbent resin when the plant component (B) is liquid, for example, when the plant component (B) is dissolved in liquid and/or water, aqueous solution, or various kinds of organic solvent at an ordinary temperature as solution; a process in which the plant component (B) is directly mixed with the water-absorbent resin so that a desired amount of the plant component (B) is added to the water-absorbent resin when the plant component (B) is powder (for example, a dry blending process is performed when mixing powders with each other); a process in which water, aqueous solution, or various kinds of organic solvent are sprayed or dropped to mixture of the plant component (B) and the water-absorbent resin obtained by directly mixing them. Note that, it is also possible to employ the following processes: a process in which the plant component (B) is added upon polymerizing the water-absorbent resin, and a process in which the plant component (B) is added to the polymerized gel.

In case of mixing the water-absorbent resin with the plant component (B) in the present embodiment, amounts of water used as required, vapor, or aqueous solution made of water and hydrophilic organic solvent vary depending on kinds and particle sizes of the water-absorbent resin. However, it is general that the amount of water is not more than 10 mass parts, preferably within a range of from 1 to 5 mass parts, with respect to 100 mass parts of the dry water-absorbent resin. Further, the amount of the hydrophilic organic solvent is not more than 10 mass parts, preferably within a range of from 0.1 to 5 mass parts, with respect to 100 mass parts of the dry water-absorbent resin.

In the present embodiment, an ordinary apparatus is used as an apparatus used in mixing the water-absorbent resin with powder and/or solution containing the plant component (B), and examples of the apparatus includes a cylindrical mixer, screw mixer, screw extruder, turbulizer, nauta mixer, V-shaped mixer, ribbon blender, double-arm kneader, fluid mixer, pneumatic conveyor mixer, rotating disc mixer, roll mixer, and convolution mixer. It does not matter whether the mixing speed is high or low.

Various kinds of inorganic powder may be further added to the water-absorbent resin and/or the water-absorbent composition as in Embodiment 1. Examples of the inorganic powder specifically include the inorganic powders exemplified in Embodiment 1. Among of them, silicon dioxide and silicate (salt) are preferable, and silicon dioxide and silicate (salt) each of which has an average particle diameter of not more than 200 μm based on measurement by Coulter Counter Method are more preferable. The amount of the inorganic powder varies depending on how the water-absorbent resin and/or water-absorbent composition is combined with the inorganic powder. However, it is possible to set the amount as in Embodiment 1. The process for mixing the water-absorbent resin and/or the water-absorbent composition with the inorganic powder is not particularly limited, and it is possible to employ the same process as in Embodiment 1, and the dry blending process is more preferable.

The production process of the water-absorbent composition according to the present embodiment may include the step for giving various functions, for example, the step of adding deodorant, antibacterial agent, fragrant materials, blowing agent, pigment, dyestuff, elasticizer, adhesive, interfacial active agent, fertilizer, oxidizer, reducer, water, saline, chelating agent, bactericide, sterilizer, bacteria eradicator, bacteriostatic agent, disinfectant, preservative, and hydrophilic macromolecule such as polyethylene glycol and polyethylene imine, hydrophobic macromolecule such as paraffin, thermoplastic resin such as polyethylene and polypropylene, and thermosetting resin such as polyester resin and urea resin. That is, the water-absorbent composition according to the present embodiment may further include the aforementioned various kinds of additive.

The water-absorbent composition obtained by the aforementioned producing process is a water-absorbent composition including the plant component (B) and the water-absorbent resin. Note that, the producing process of the water-absorbent composition of the present embodiment is not particularly limited to the foregoing processes.

The water-absorbent composition of the present embodiment is a water-absorbent composition including the plant component (B) and the water-absorbent resin.

In the water-absorbent composition of the present embodiment, when the plant component (B) is the semi-fermented tea extract and/or the fermented tea extract as described in Embodiment 1, not less than ⅓ and less than ⅘, preferably not less than ⅓ and less than ¾, more preferably not less than ⅓ and less than 7/10, still more preferably ⅓ to ⅔, further more preferably ⅓ to ⅗ of all molar quantities of the acid group (acid group in the water-absorbent resin which is substantially a main element), more preferably from ⅓ to ⅗ of all molar quantities of the acid group are neutralized. Specifically, when the water-absorbent resin is mainly made of acrylic acid, not less than ⅓ and less than ⅘, preferably not less than ⅓ and less than ¾, more preferably ⅓ to 7/10, still more preferably ⅓ to ⅔, further more preferably ⅓ to ⅗ of all molar quantities of acrylic acid is acrylate.

Further, in the water-absorbent composition of the present embodiment, when the plant component (B) is a plant component (B) other than the semi-fermented tea extract and/or the fermented tea extract, not less than ⅓ and less than ¾, preferably ⅓ to 7/10, more preferably ⅓ to ⅔, still more preferably ⅓ to ⅗ of all molar quantities of acid group thereof (acid group in the water-absorbent resin which is substantially a main element) is neutralized. Specifically, when the water-absorbent resin is made mainly of acrylic acid, not less than ⅓ and less than ¾, preferably not less than ⅓ and less than 7/10, more preferably ⅓ to ⅔, still more preferably ⅓ to ⅗ of all molar quantities of acrylic acid is acrylate.

Further, the process of the present embodiment for producing the water-absorbent composition, being particulate, which is made mainly of a water-absorbent resin (A) having a cross-linking structure obtained by polymerizing an unsaturated monomer containing acid groups, wherein (1) not less than ⅓ and less than ¾ (however, when the plant component (B) described later is selected from the semi-fermented tea extract and/or the fermented tea extract, not less than ⅓ and less than ⅘) of all molar quantities of an acid group is neutralized, and (2) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and (3) a plant component (B) containing at least one kind selected from polyphenol, flavones, and caffeine is included, and the process includes the steps of: polymerizing the unsaturated monomer containing acid groups, in which not less than ⅓ and less than ¾ (however, when the plant component (B) described later is selected from the semi-fermented tea extract and/or the fermented tea extract, not less than ⅓ and less than ⅘) of all molar quantities of the acid group are neutralized, so as to obtain the water-absorbent resin having the cross-linking structure; adjusting a particle size of thus obtained water-absorbent resin so that the amount of the particles whose particle diameter is less than 850 μm and not less than 150 μm is not less than 90 mass % with respect to the whole; and mixing the water-absorbent resin whose particle size has been adjusted with the plant component (B) containing at least one kind selected from polyphenol, flavones, and caffeine. Note that, the foregoing production process may be arranged so that: the step of obtaining the water-absorbent resin brings about the water-absorbent resin having a cross-linking structure obtained by polymerizing an unsaturated monomer containing acid groups which has a desired neutralization rate in advance, i.e., an unsaturated monomer containing acid groups in which not less than ⅓ and less than ¾ of all molar quantities of acid group (however, in case where the plant component (B) described later is selected from the semi-fermented tea extract and/or the fermented tea extract, not less than ⅓ and less than ⅘ of all molar quantities of acid group) is neutralized. Also, the water-absorbent resin having the foregoing properties may be obtained as follows: after polymerising the unsaturated monomer containing acid groups which has not been neutralized or has a neutralization rate lower than the desired neutralization rate, the polymerized resultant is neutralized (i.e., post-neutralized) so that the desired neutralization rate is realized.

In the present embodiment, an acrylic acid portion which has not been neutralized enables a basic odious element (ammonia, amines, for example) to be neutralized. Further, the plant component (B) is known for its deodorant effect with respect to the odious element, but the present inventors found the following characteristics: when the plant component (B) is the semi-fermented tea extract and/or the fermented tea extract, the deodorant effect of the plant component (B) is greatly improved by the synergy effect of the plant component (B) and the water-absorbent resin in which not less than ⅓ and less than ⅘, preferably not less than ⅓ and less than ¾, more preferably not less than ⅓ and less than 7/10, still more preferably ⅓ to ⅔, further preferably ⅓ to ⅗ of the unsaturated monomer containing acid groups (acrylic acid) is acrylate, or when the plant component (B) is a plant extract other than the semi-fermented tea extract and/or the fermented tea extract, the deodorant effect of the plant component (3) is greatly improved by the synergy effect of the plant component (B) and the water-absorbent resin in which not less than ⅓ and less than ¾, preferably not less than ⅓ and less than 7/10, more preferably ⅓ to ⅔, still more preferably ⅓ to ⅗ of the unsaturated monomer containing acid groups (acrylic acid) is acrylate.

Further, the present inventors found that: when the plant component (B) is the semi-fermented tea extract and/or the fermented tea extract, the deodorant effect with respect to a sulfuric odious element, such as hydrogen sulfide and methyl mercaptan, which causes putrid odor, is improved by the water-absorbent composition including the plant component (B) and the water-absorbent resin in which not less than ⅓ and less than ⅘, preferably not less than ⅓ and less than ¾, more preferably not less than ⅓ and less than ⅘, still more preferably ⅓ to ⅔, further more preferably ⅓ to ⅗ of the unsaturated monomer containing acid groups (acrylic acid) is acrylate, or when the plant component (B) is a plant component (B) other than the semi-fermented tea extract and/or the fermented tea extract, the deodorant effect with respect to a sulfuric odious element, such as hydrogen sulfide and methyl mercaptan, which causes putrid odor, is improved by the water-absorbent composition including the plant component (B) and the water-absorbent resin in which not less than ⅓ and less than ¾, preferably not less than ⅓ and less than 7/10, more preferably ⅓ to ⅔, still more preferably ⅓ to ⅗ of the unsaturated monomer containing acid groups (acrylic acid) is acrylate, and the deodorant effect is kept even when the water-absorbent composition is left for a long time with it actually containing urine while being practically used in a diaper etc. How the effect is brought about has not been clarified, but the cause thereof may be as follows: when the plant component (B) is the semi-fermented tea extract and/or the fermented tea extract, the deodorant effect is brought about, or the plant component (B) is stabilized by the condition under which not less than ⅓ and less than ⅘, preferably not less than ⅓ and less than ¾, more preferably not less than ⅓ and less than 7/10, still more preferably ⅓ to ⅔, further more preferably ⅓ to ⅗ of the unsaturated monomer containing acid groups is acrylate. Further, the cause thereof may be as follows: when the plant component (B) is a plant extract other than the semi-fermented tea extract and/or the fermented tea extract, the deodorant effect of the plant component (B) is caused, or the plant component (B) is stabilized by the condition under which not less than 1/3 and less than 3/4, preferably not less than 1/3 and less than 7/10, more preferably 1/3 to 2/3, still more preferably 1/3 to 3/5 of the unsaturated monomer containing acid groups is acrylate.

Further, the water-absorbent composition according to the present embodiment is characterized in that the amount of particles whose particle diameter is less than 850 μm and not less than 150 μm is not less than 90 mass % with respect to the whole and the amount of particles whose particle diameter is not less than 300 μm is 60 mass % with respect to the whole.

The water-absorbent resin used in the present embodiment has an acidic group (carboxyl group), so that a basic odious element such as ammonia is effectively neutralized for example. Although it is considered that a surface area of the water-absorbent resin (and water-absorbent composition) is larger as the particle diameter is smaller and a larger surface area is more advantageous in neutralizing the basic odious element, the present inventors found it advantageous to use particles having a specific particle diameter in removing the odious element when it is practically used (for example, it is used as gelatinizer of urine, such as a paper diaper), as a result of earnest study.

How the effect is brought about has not been clarified, but a gel state of the water-absorbent composition may have any influence for example. When the particle diameter is too small, the absorption rate is too fast, so that this may cause a gel-block phenomenon which prevents liquid containing the odious element from reaching the water-absorbent composition. Further, when the particle diameter is too large, the absorption rate is too slow, so that the odious element may evaporate from the liquid containing the odious element.

Further, it is preferable that the water-absorbent composition according to the present embodiment is arranged so that: the absorption capacity (CRC) in case where 0.90 mass % of physiological saline is absorbed without load for 60 minutes is not less than 30 g/g, and the diffusing absorption capacity (DAP) in case where 0.90 mass % of physiological saline is absorbed at 1.9 kPa for 60 minutes is not less than 24 g/g. Note that, as the upper limit of the absorption capacity (CRC) is higher, it becomes more preferable, but 60 g/g is preferable since this condition weakens the gel strength and tends to bring about the gel blocking phenomenon. Further, as the upper limit of the diffusing absorption capacity (DAP) is higher, it becomes more preferable, but 50 g/g is preferable in terms of the functional balance with the absorption capacity (CRC). The CRC is preferably not less than 32 g/g, more preferably not less than 34 g/g. Further, the DAP is preferably not less than 26 g/g, more preferably not less than 28 g/g.

In case where the absorption capacity (CRC) is less than 30 g/g, when the water-absorbent composition is used in an absorbent described later and/or an absorbing product (for example, a paper diaper and the like), an absorbing power for absorbing liquid containing the odious element such as urine is deteriorated, so that this brings about problems such as leakage and skin fit in practically using a paper diaper, and an ability for removing odor is insufficient. Further, in practically using the paper diaper etc., a weight of a paper diaper wearer is sometimes laid on the absorbent and/or the absorbing product.

In case where the dispersing absorption capacity (DAP) is less than 24 g/g, when a load such as a weight is laid on the water-absorbent composition, a liquid diffusing power and an absorbing power with respect to the liquid containing the odious element such as urine are deteriorated, so that the liquid is prevented from being diffused in the absorbent and/or the absorbing product, thereby causing the liquid to be blocked. Thus, the liquid does not entirely spread in the water-absorbent composition, so that this may bring about problems such as leakage and skin fit in practically using the paper diaper, and an ability for removing the odor may be insufficient.

Further, ranges of a shape, a dry water-absorbent resin (moisture content), a water extractable, and the like of the water-absorbent composition of the present embodiment are as described above, and the water extractable is preferably not more than 25 mass %, more preferably not more than 20 mass %, still more preferably not more than 15 mass %. Further, a coloring state of the water-absorbent composition of the present embodiment ranges from 0 to 15, preferably from 0 to 13, more preferably from 0 to 10, most preferably from 0 to 5, in terms of a YI value (Yellow Index: see European Patents. No. 942014 and No. 1108745). Further, a residual monomer is 400 ppm, more preferably 300 ppm.

The water-absorbent composition of the present embodiment is arranged so that: the amount of particles whose particle diameter is less than 850 μm and not less than 150 μm is not less than 90 mass % with respect to the whole and the amount of particles whose particle diameter is not less than 300 μm is 60 mass % with respect to the whole, preferably the amount of the particles whose particle diameter is less than 850 μm and not less than 150 μm is not less than 95 mass %, more preferably not less than 98 mass % with respect to the whole. Further, the particles whose particle diameter is not less than 300 μm is more preferably 65 mass %, still more preferably 70 mass %, particularly preferably not less than 75 mass %. Further, the mass average particle diameter of the water-absorbent resin ranges preferably from 200 to 700 μm, more preferably from 300 to 600 μm, still more preferably from 400 to 500 μm.

That is, the present inventors found that the deodorant effect of the present invention cannot be achieved when the amount of the particles whose particle diameter is not less than 300 μm is less than 60 mass %. The present inventors found that: a specific surface area becomes smaller as the particle diameter becomes larger, but, to the surprise, the combination of foregoing materials (1) to (3) improves the deodorant effect by decreasing the specific surface area thereof, which is caused by increasing the particle diameter.

(IV) Absorbent and/or Absorbing Product

The absorbent of the present embodiment includes the water-absorbent composition, recited in (III), according to the present embodiment.

Further, the absorbent of the present embodiment includes: the particulate water-absorbent composition made mainly of the water-absorbent resin (A) having a cross-linking structure obtained by polymerizing unsaturated monomer containing acid groups; and a hydrophilic fiber, and the water-absorbent composition is such that: (1) not less than 1/3 and less than 3/4, preferably not less than 1/3 and less than 7/10, more preferably 1/3 to 2/3, further preferably 1/3 to 3/5 of all molar quantities of the acid group are neutralized, and (2) the amount of particles whose particle diameter is less than 850 μm and not less than 150 μm is not less than 90 mass % with respect to the whole and the amount of particles whose particle diameter is not less than 300 μm is not less than 60 mass % with respect to the whole, and the absorbent further includes (3) the plant component (B) containing at least one kind selected from polyphenol, flavones, and caffeine.

Further, the absorbent of the present embodiment includes: the particulate water-absorbent composition made mainly of the water-absorbent resin (A) having a cross-linking structure obtained by polymerizing unsaturated monomer containing acid groups; and a hydrophilic fiber, and the water-absorbent composition is such that: (1) not less than ⅓ and less than ⅘, preferably not less than ⅓ and less than ¾, more preferably not less than ⅓ and less than 7/10, still more preferably ⅓ to ⅔, further more preferably ⅓ to ⅗ of all molar quantities of the acid group are neutralized, and (2) the amount of particles whose particle diameter is less than 850 µm and not less than 150 µm is not less than 90 mass % with respect to the whole and the amount of particles whose particle diameter is not less than 300 µm is not less than 60 mass % with respect to the whole, and the absorbent further includes (3) a semi-fermented tea extract and/or a fermented tea extract (i.e., at least one kind of polyphenol selected from a group of the semi-fermented tea extract and the fermented tea extract) as the plant component (B) containing at least one kind selected from polyphenol, flavones, and caffeine.

That is, in the absorbent of the present embodiment, the plant component (B) is essentially added and included in the elements of the absorbent. The plant component (B) may be added internally to the water-absorbent composition, or may be provided separately from the water-absorbent composition. For example, the plant component (B) may be added to and included in a fiber base material, such as a hydrophilic fiber, other than the water-absorbent composition, but it is more preferable to add the plant component (B) to the water-absorbent composition in terms of the effect.

The water-absorbent resin (A) of each absorbent is preferably arranged so that its surface portion and/or periphery thereof is treated by a cross-linking agent.

Further, in the present embodiment, it is preferable that the absorbent is an absorbent molded by using mainly the water-absorbent resin and the hydrophilic fiber. Although it is possible to obtain such absorbent by molding the water-absorbent composition of the present embodiment and the hydrophilic fiber into a sheet shape or a cylindrical shape, the absorbent may be obtained by using the foregoing water-absorbent resin (A), the plant component (B), and the hydrophilic fiber.

Also in the present embodiment, the absorbent may be arranged so that the water-absorbent composition is sandwiched between fibers other than the hydrophilic fibers such as tissue paper, or may be arranged so that the water-absorbent composition is merely coagulated by the adhesive and the like, as in Embodiment 1. That is, also the absorbent of the present embodiment may be arranged so that the core concentration, i.e., the amount of the included water-absorbent composition with respect to a total mass of the water-absorbent composition and the hydrophilic fiber is 100 mass %. However, when the absorbent includes the hydrophilic fiber, the upper limit of the amount (core concentration) of the added water-absorbent composition with respect to a total mass of the water-absorbent composition and the hydrophilic fiber is within a range of less than 100 mass %, preferably within a range of from 10 to 90 mass %, more preferably from 20 to 90 mass %, further preferably from 25 to 80 mass %. When the core concentration is less than 10 mass %, the amount of the water-absorbent composition is little, so that the sufficient deodorant effect sometimes is not provided to a whole diaper. Thus, this is not preferable. Further, when the core concentration exceeds 90 mass % (that is, the amount of the included hydrophilic fiber with respect to the total mass of the water-absorbent composition and the hydrophilic fiber is less than 10 mass %), it is impossible to sufficiently exhibit the effect obtained by using the hydrophilic fiber. It is possible to easily produce the absorbent, for example, by blending the hydrophilic fiber, the water-absorbent composition, if necessary, other fiber base material and adhesive together, or by sandwiching the water-absorbent composition by the fiber base materials such as the hydrophilic fiber.

Further, the absorbing product of the present embodiment includes the aforementioned absorbent of the present embodiment, a surface sheet having liquid permeability, and a back sheet having liquid impermeability.

The producing process of the absorbing product of the present embodiment is such that: the absorbent (absorbent core) is made by blending the fiber base material and the water-absorbent composition together, or by sandwiching the water-absorbent composition by the fiber base materials, and the absorbent core is sandwiched by a base material having the liquid permeability (surface sheet) and a base material having the liquid impermeability (back sheet), and an elastic member, a diffusing layer, an adhesive tape, and the like are provided, thereby obtaining the absorbing product, particularly an adult diaper or a sanitary napkin. Such absorbent core is formed in a compression manner so that the density ranges from 0.06 to 0.50 g/cm$^3$ and the capacity of scale ranges from 0.01 to 0.20 g/cm$^2$ for example. Note that, examples of the fiber base material include: a hydrophilic fiber such as crushed wood pulp; cotton linter and cross-linking cellulose fabric; rayon; cotton; wool; acetate; and vinylon. It is preferable to perform an air-laid process with respect to them.

The water-absorbent composition of the present embodiment can provide the superior deodorant function to the absorbing product and exhibits the superior deodorant property and the superior absorbent characteristic for a long time. Examples of such absorbing product specifically include sanitary materials such as an adult diaper being developed recently, a baby diaper, a sanitary napkin, a so-called incontinence pad, but the use is not limited to these materials. The water-absorbent composition which exists in the absorbing product has the superior deodorant characteristic, and returns little liquid, and realizes good dry touch, so that it is possible to largely reduce the load of the wearer and care givers. Further, also the water-absorbent composition of the present embodiment can be used not only as the sanitary material but also as a deodorant for example as in Embodiment 1.

The following Examples and Comparative Examples will further detail the present invention, but the present invention is not limited to these Examples. Note that, properties of the water-absorbent resin (or water-absorbent composition) and the absorbing products were measured in the following manner.

(a) Absorption Capacity (CRC)

0.20 g (W1 (g)) of water-absorbent resin (or water-absorbent composition) was evenly placed in a nonwoven bag (60 mm×60 mm). Then, the nonwoven bag was placed in 100 g of an aqueous 0.9 mass % sodium chloride solution (physiologic saline) whose temperature was adjusted to 25° C. The nonwoven bag was removed from the aqueous solution 60 minutes later, and centrifuged at 250 G for three minutes using a centrifugal separator. The mass W3 (g) of the nonwoven bag was measured. The same test was performed using an empty bag containing no water-absorbent resin (or water-absorbent composition), and the mass W2 (g) of the empty bag was measured. The absorption capacity (g/g) was calculated from the mass W1, W2, and W3 according to the following equation.

$$\text{Absorption capacity}(g/g) = (W3(g) - W2(g))/W1(g)$$

(b) Absorbing Power Under a Load and Absorption Index Under a Load

A measuring apparatus for use in measuring the absorbing power under a load is first explained briefly with reference to FIG. 1.

As illustrated in FIG. 1, the measuring apparatus includes a container 1, filter paper 2 (10 sheets of filter paper, "No. 2" made by Advantech, whose diameter is 90 mm), and a measuring section 3.

The container 1 contains 25 g of synthetic urine 4 whose temperature was adjusted to 25° C. (synthetic urine was made up of: 97.1 g of deionized water, 1.9 g of urea, 0.8 g of sodium chloride, 0.1 g of magnesium chloride hexahydrate, and 0.1 g of calcium chloride).

The measuring section 3 includes a bearing cylinder 5, a metal gauze 6 attached to the bottom of the bearing cylinder 5, and a weight 7. In the measuring section 3, the bearing cylinder 5 (i.e., the metal gauge 6) is placed in this order on the paper filter 2, and the weight 7 is placed inside the bearing cylinder 5, i.e., on the metal gauge 6. An inside diameter of the bearing cylinder 5 is 60 mm. The metal gauze 6 was made of stainless steel and is 400 mesh (38 μm in mesh). A total mass of the bearing cylinder 5 and the metal gauze 6 was adjusted to 62 g. A predetermined amount of water-absorbent resin (or water-absorbent composition) was evenly spread over the metal gauze 6. The mass of the weight 7 was adjusted so that a load of 1.96 kpa was evenly applied to the metal gauze 6, i.e., to the water-absorbent resin (or water-absorbent composition).

The absorbing power under a load and absorption index under a load were measured using a measuring apparatus of the above-mentioned structure. The following description will discuss the measuring method.

(1) Absorbing Power Under a Load

First, the filter paper 2 was placed on the container 1. Next, 25 g of the synthetic urine 4 whose temperature was adjusted to 25° C. was placed in the container 1 so that the filter paper 2 absorbed the synthetic urine 4. At the same time as placing the filter paper 2 on the container 1, 1.0 g of the water-absorbent resin (or water-absorbent composition) was evenly spread inside the bearing cylinder 5, i.e., on the metal gauge 6, and the weight 7 was then placed on the water-absorbent resin (or water-absorbent composition). Mass (W4) of the bearing cylinder 5 containing the water-absorbent resin (or water-absorbent composition) and the weight 7 was measured.

Next, the bearing cylinder 5 whereupon the water-absorbent resin (or water-absorbent composition) and the weight 7 were placed, was placed on the center of the filter paper 2. Then, the synthetic urine was absorbed by the water-absorbent resin (or water-absorbent composition) for 60 minutes after the placement of the bearing cylinder 5 on the filter paper 2. 60 minutes later, mass (W5) of the bearing cylinder 5 containing the water-absorbent resin (water-absorbent composition) having absorbed the synthetic urine and the weight 7 was measured. The absorbing power under a load (g/g) of the water-absorbent resin left for 60 minutes after the initiation of the absorption was calculated according to the following equation.

Absorbing power under a load(g/g)=($W5$(g)−$W4$(g))/1.0(g)

(2) Initial Absorbing Power Under a Load

The same process as in the absorbing power under a load calculated in the foregoing measurement (1) was performed except that the synthetic urine was absorbed by the water-absorbent resin (or water-absorbent composition) with the passage of time over 3 minutes. That is, the synthetic urine was absorbed by the water-absorbent resin (or water-absorbent composition) with the passage of time over 3 minutes, and 3 minutes later, mass (W6) of the bearing cylinder 5 containing the water-absorbent resin (water-absorbent composition) having absorbed the synthetic urine and the weight 7 was measured. The absorbing power under a load (g/g) of the water-absorbent resin left for 3 minutes after the initiation of the absorption was calculated according to the following equation.

Initial absorbing power under a load(g/g)=($W6$(g)−$W4$(g))/1.0(g)

(3) Absorption Index Under a Load

The absorption index under a load (g/g) was calculated from the absorbing power under a load calculated in the foregoing measurement (1) and the initial absorbing power under a load calculated in the foregoing measurement (2) according to the following equation.

Absorption index under a load(g/g)=Initial absorbing power under a load(g/g)+Absorbing power under a load(g/g)

(c) Absorption Rate 50 g of blue physiological saline (composition thereof is described as follows) whose temperature was adjusted to 30° C. and a white stirrer (Teflon (trade name), mentioned in Union Catalogue Version 2,000 published by FLON INDUSTRY CO., LTD., Teflon (trade name) stirrer SA type, product No. SA-40, total length 40 mm×diameter 8 mm) were placed in a beaker of 100 ml (TOP beaker CAT. No. 501, based on JIS R-3503, which is mentioned in GENERAL CATALOGUE A-7000 published by Sogo Rikagaku Glass Industry Co., Ltd.: entire length×height=55 (mm)×70 (mm)) in advance, and the physiological saline was stirred by a magnetic stirring device at a speed of 600 rpm. When 2.0 g of the water-absorbent resin (or water-absorbent composition) was added to the physiological saline, gelation of the test solution was promoted, and a swirl was diminished, so that the test solution surrounded the stirrer. A time (second) since the water-absorbent resin had been added to the test solution until the stirrer was surrounded by the test solution (period until the rotating stirrer that had been seen was hidden by the protuberant swirl that had almost disappeared) was measured, and the time was regarded as the absorption rate.

The blue physiological saline is composed of: 991 mass parts of deionized water, 9 mass parts of sodium chloride, and 0.02 mass parts of food additive edible Brilliant Blue. (food additive edible brilliant blue: benzyl-ethyl-[4'-(4"-benzyl ethyl amino)-diphenyl methylene)-2', 5-cyclohexa dienylidene]-ammonium-2''',3,3'''-disodium trisulfonic acid; brilliant blue FCF; CI No. 42090; CI Food blue 2)

(d) Mass Average Particle Diameter of Water-Absorbent Resin 10 g of the water-absorbent resin was sieved in a shaking manner by a sieve shaker (IIDA SIEVE SHAKER ES-65 TYPE, made by IIDA SEISAKUSHO CO., LTD.) for 5 minutes for classification using a JIS standard sieve (850 μm, 600 μm, 300 μm, 150 μm, 106 μm) whose inside diameter is 75 mm, and each particle size on each sieve (850 μm-on particles/850 μm-pass and 600 μm-on particles/600 μm-pass and 300 μm-on particles/300 μm-pass and 150 μm-on particles/150 μm-pass and 106 μm-on particles/106 μm-pass particles) was measured in terms of mass. Note that, the "-on particles" means particles which were not allowed to pass through the sieve having the foregoing inside diameter and remained on the sieve. That is, the "-on particles" means particles whose particle diameter is larger than the inside diameter of the sieve. The "-pass particles" means particles which passed through the sieve having the foregoing inside diameter. That is, the "-pass particles" means particles whose particle diameter is smaller than the inside diameter of the sieve. Further, particle size distribution of measured particle sizes was plotted on a logarithmic probability paper, thereby calculating a mass average particle diameter (D50).

(e) Deodorant Test (Water-Absorbent Resin or Water-Absorbent Composition)

Deodorant Test A

Examples 1 to 7 and Comparative Examples 1 to 7

50 ml of mixture of urine gathered from 10 adults was placed in a 120 ml-polypropylene cup (Pack Ace made by TERAOKA CORPORATION, nozzle diameter (mm)×bottom diameter (mm)×height (mm)=58×54×74). Then, 2.0 g of the water-absorbent resin (or water-absorbent composition) was added to the urine mixture so as to form a swelling gel. The urine was used within two hours from excretion. This container was covered with a lid, and a temperature of the swelling gel was kept at 37°. In one minute (initial state), three hours, and six hours after the urine had absorbed, the lid was opened, and 20 adults sniffed the smell of the swelling gel as panelists at a position 3 cm above the cup, so as to judge the deodorant effect thereof.

They made 1-to-5-scale evaluations such as 1: odorless, 2: hardly perceptible, 3: perceptible but sufferable, 4: strong smell, and 5: overpowering smell. The evaluations were added, and then averaged. Note that, the same operation was performed except using only the urine without adding the water-absorbent resin (or water-absorbent composition), and the deodorant effect was evaluated based on the smell of the urine regarded as being 5, i.e., a standard.

Deodorant Test B

Examples 8 to 25 and Comparative Examples 8 to 10

The swelling gel was formed in the same manner as in the foregoing test except that 50 ml of mixture of urine gathered from 20 adults was placed in a container (120 ml-polypropylene cup). This container was covered with a lid, and a temperature of the swelling gel was kept at 37°. When six hours passed after the urine had absorbed, the lid was opened, and 20 adults judged the deodorant effect thereof in the same manner as in the foregoing test.

They made 0-to-5-scale evaluations such as 0: odorless, 1: barely perceptible, 2: perceptible but sufferable, 3: easily perceptible, 4: strong smell, and 5: overpowering smell. The evaluations were added, and then averaged. Note that, the same operation was performed except using only the urine without adding the water-absorbent resin (or water-absorbent composition), and the deodorant effect was evaluated based on the smell of the urine regarded as being 5, i.e., a standard.

(f) Deodorant Test (Absorbing Product)

Deodorant Test C

Examples 1 to 7 and Comparative Examples 1 to 7

50 mass parts of the water-absorbent resin (or water-absorbent composition) and 50 mass parts of crushed wood pulp were mixed in a drying manner using a mixer. Next, the obtained mixture was deposited, in an airy-formation manner, on a wire screen which is 400 mesh (38 μm in mesh), using a batch type airy formation device, so as to form the mixture of 120 mm×400 mm. Further, this web was pressed at a pressure of 196.14 kPa for five seconds, thereby obtaining an absorbent body whose scale was approximately 0.047 g/cm$^2$.

Next, a back sheet (liquid-impermeable sheet), made of liquid-impermeable polypropylene, which has a so-called leg gather, the absorbent, and a top sheet (liquid-permeable sheet) made of liquid-permeable polypropylene were made to adhere to each other in this order using double face tapes, and two so-called tape fasteners were made to adhere to this adhesive material, thereby obtaining an absorbing product (that is, a paper diaper). Mass of the absorbing product was 46 g.

As monitors, 10 babies aged one wore the absorbing products overnight, and the absorbing products were collected the next day. An absorbent portion (so-called core portion) made of the water-absorbent resin (or water-absorbent composition) and the wood pulp was cut into a size of 10 cm×10 cm, and was placed in a 250 ml polypropylene cup having a lid (Pack Ace, made by TERAOKA CORPORATION, nozzle diameter (mm)×bottom diameter (mm)×height (mm)=69× 63×97). This container was covered with the lid, and a temperature of the absorbent body was kept at 37° C. In one hour, the lid was opened, and 20 adults sniffed the smell of the absorbing product as panelists at a position 3 cm above the cup, so as to judge the deodorant effect thereof. They made 1-to-5-scale evaluations such as 1: odorless, 2: hardly perceptible, 3: perceptible but sufferable, 4: strong smell, and 5: overpowering smell. The evaluations were added, and then averaged.

Deodorant Test D

Examples 26 to 35 and Comparative Examples 11 to 13

The obtained absorbing product was cut into a size of 10 cm×10 cm, and was placed in a 250 ml polypropylene cup having a lid. 20 g of mixture of urine gathered from 20 adults was placed in this container. The container was covered with the lid, and a temperature of whole the container was kept at 37° C. When six hours passed, the lid was opened, and 20 adults sniffed the smell of the absorbing product as panelists at a position 3 cm above the cup, so as to judge the deodorant effect thereof.

They made 0-to-5-scale evaluations such as 0: odorless, 1: barely perceptible, 2: perceptible but sufferable, 3: easily perceptible, 4: strong smell, and 5: overpowering smell. The evaluations were added, and then averaged. Note that, the same operation was performed except using only the urine without adding the water-absorbent resin (or water-absorbent composition), and the deodorant effect was evaluated based on the smell of the urine regarded as being 5, i.e., a standard.

(g) Diffusing Absorption Capacity (DAP)

The diffusing absorption capacity is a property value for evaluating a water-absorbent amount in consideration for diffusing power of the aqueous solution under such condition that a basis weighing of the water-absorbent resin (or water-absorbent composition) is high and resin particles adhere to each other due to an external force.

As to the diffusing absorption capacity of the water-absorbent resin (or water-absorbent composition), mass W7 (g) of physiological saline absorbed by the water-absorbent resin (or water-absorbent composition) for 60 minutes was measured by a measuring apparatus and a measuring procedure that are recited in Japanese Unexamined Patent Publication No. 57311/1996 (Tokukaihei 8-57311) (Publication date: Mar. 5, 1996).

The diffusing absorption capacity (g/g) of the water-absorbent resin (or water-absorbent composition) in 60 minutes after the initiation of the absorption was calculated from the mass W7 according to the following equation.

Diffusing absorption capacity(g/g)=$W7$(g)/mass(g) of water-absorbent resin(or water-absorbent composition)

The following is detail description thereof. The diffusing absorption capacity was measured by using a measuring apparatus shown in FIG. 2 and FIG. 3.

Figure 2:
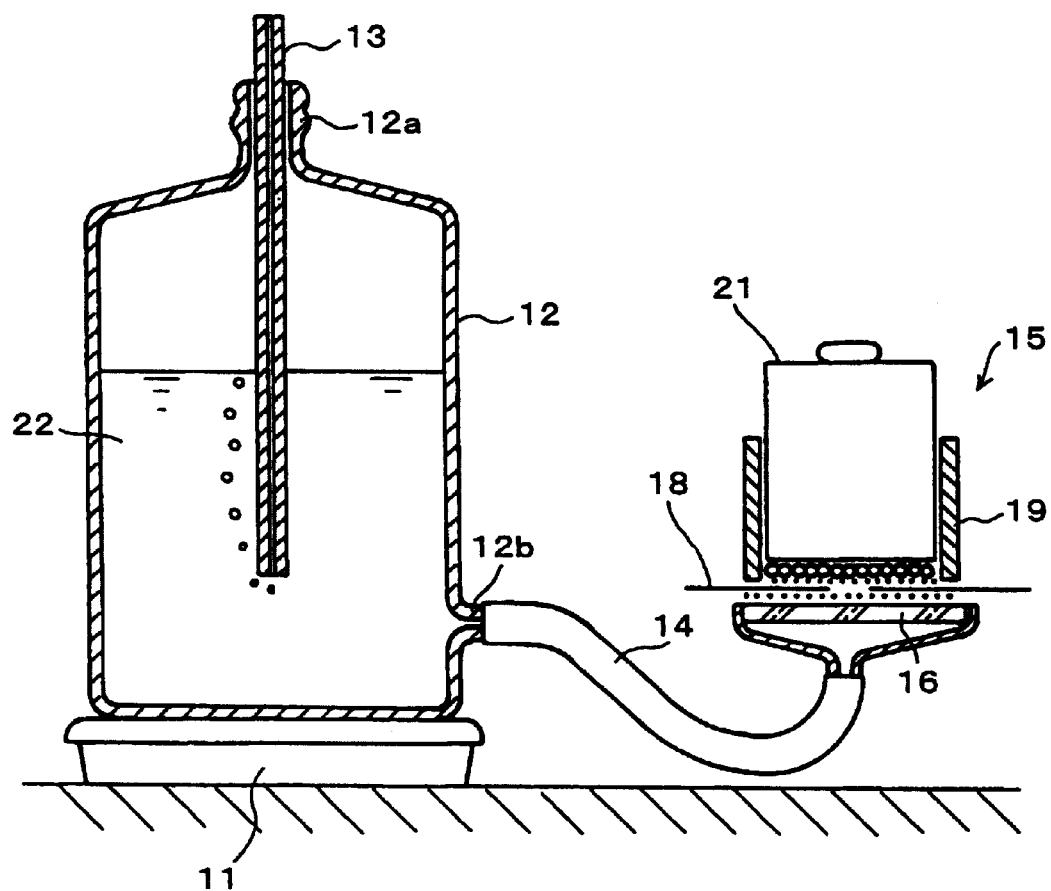
FIG. 2 is a cross sectional view schematically showing a measuring apparatus used in measuring a diffusing absorption capacity which indicates one performance of the water-absorbent resin (or water-absorbent composition).

As shown in FIG. 2, the apparatus for measuring the diffusing absorption capacity is equipped with: a scale 11; a container 12, provided on the scale 11, which has a predetermined capacity; an outside air suction pipe 13; a conduit 14; a glass filter 16; and a measuring section 15 provided on the glass filter 16. The container 12 has an opening 12a on a top portion thereof, and has an opening 12b on a side portion thereof. The outside air suction pipe 13 is put into the opening 12a, and the conduit 14 is provided on the opening 12b. Further, a predetermined amount of physiological saline 22 is placed in the container 12. A lower end of the outside air suction pipe 13 is dipped in the physiological saline. A diameter of the glass filter 16 is 70 mm. The container 12 and the glass filter are connected with each other by the conduit 14. The container 12 and the glass filter 16 are fixed at a position slightly higher than the lower end of the outside air suction pipe 13.

Figure 3:
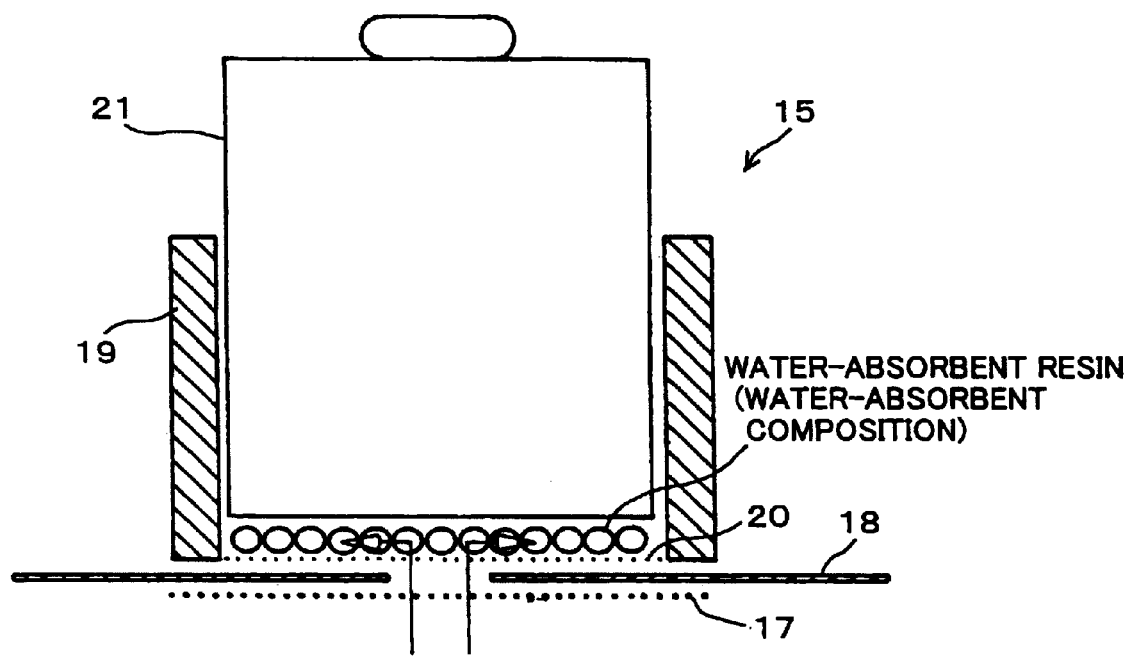
FIG. 3 is a cross sectional view showing an important part of the measuring apparatus shown in FIG. 2.

As shown in FIG. 3, the measuring section 15 has a filter paper 17, a sheet 18, a bearing cylinder 19, a metal gauze 20 attached to a bottom portion of the bearing cylinder 19, and a weight 21. In the measuring section 15, the filter paper 17, the sheet 18, the bearing cylinder 19 (i.e., the metal gauze 20) are placed in this order on the glass filter 16, and the weight 21 is placed inside the bearing cylinder 19, i.e., on the metal gauze 20. The sheet 18 is made of polyethylene terephthalate (PET), and has an opening whose diameter is 18 mm so as to be formed in a doughnut shape whose thickness is 0.1 mm. An inside diameter of the bearing cylinder 19 is 60 mm. The metal gauze 20 is made of stainless, and is 400 mesh (38 μm in mesh). Further, a predetermined amount of the water-absorbent resin is evenly dispersed on the metal gauze 20. The weight 21 is adjusted so that a load of 20 g/cm² can be evenly added to the metal gauze 20, i.e., the water-absorbent resin.

The diffusing absorption capacity was measured by the measuring apparatus of the foregoing structure. The measuring method is described as follows.

First, predetermined preparative operations were performed in such manner that: a predetermined amount of physiological saline 22 is placed in the container 12, and the outside air suction pipe 13 is put into the container 12. Next, the filter paper 17 is placed on the glass filter 16, and the sheet 18 is placed on the filter paper 17 so that its opening is positioned in a center of the glass filter 16. At the same time as placing the sheet 18 on the filter paper 17, 1.5 g of the water-absorbent resin (preferably, the water-absorbent resin (or water-absorbent composition) whose particle diameter was adjusted to 300 μm to 500 μm by performing operations such as classification) was evenly spread inside the bearing cylinder 19, i.e., on the metal gauze 20, and the weight 21 was then placed on the water-absorbent resin (or water-absorbent composition).

Next, the metal gauze 20, i.e., the bearing cylinder 19 whereupon the water-absorbent resin (or water-absorbent composition) and the weight 21 were placed, was placed on the sheet 18 so that a center of the metal gauze 20 is positioned in the center of the glass filter 16.

Further, mass W7 (g) of the physiological saline 22 absorbed by the water-absorbent resin (water-absorbent composition) for 60 minutes since the bearing cylinder 19 had been placed on the sheet 18 was measured by the scale 11. Note that, the physiological saline 22 was absorbed by the water-absorbent resin while evenly diffusing crosswise with respect to the water-absorbent resin (or water-absorbent composition) after passing through the opening of the sheet 18.

Then, the diffusing absorption capacity (g/g) in 60 minutes after the initiation of the absorption was calculated from the mass W7 in accordance with the following equation.

(h) Evaluation of Absorbing Product (Returning Amount)

The absorbing product obtained in Examples described later was entirely loaded at 1.96 kPa, and was left at a room temperature. 75 g of physiologic saline whose temperature was adjusted to 37° C. (NaCl aqueous solution of 0.9 mass %) was poured from a cylinder, whose diameter was 50 mm and height was 100 mm, to a center of the absorbing product. After leaving the absorbing product with it loaded for three hours, thirty paper towels ("Kitchen Towel Extra-Dry", made by Oji Paper Co., Ltd., which had been cut into a size of 120 mm×450 mm) were placed on the absorbing product, and the towels were loaded at 37 g/cm² (3.63 kPa) for a minute. Then, an amount of liquid which had returned to the paper towels was measured.

Referential Example 1

4.00 g of polyethylene glycol diacrylate (average additional molar number of ethylene oxide was 8) was dissolved in 5500 g of sodium acrylate aqueous solution (monomer concentration was 33 mass %) whose neutralization rate was 75 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization is initiated approximately one minute later. Then, the polymerization was performed at 30° C. to 80° C. for 60 minutes after the initiation of the polymerization, so that hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified by the metal gauze which is 20 mesh (850 μm in mesh) and blended, thereby obtaining an irregularly crushed water-absorbent resin (a) whose mass average particle diameter is 295 μm.

A surface-cross-linking agent constituted of one mass part of propylene glycol, 0.05 mass parts of ethylene glycol diglycidyl ether, 3 mass parts of water, and one mass part of isopropyl alcohol was mixed with 100 mass parts of the obtained water-absorbent resin (a). The mixture was heated at 210° C. for 50 minutes, thereby obtaining a water-absorbent resin (1). An absorption capacity of the water-absorbent resin (1) was 33 (g/g), and an absorption index under a load thereof was 21 (g/g), and an absorption rate thereof was 37 seconds. Further, a mass average particle diameter of the water-absorbent resin (1) was 295 μm, not largely different from the aforementioned water-absorbent resin.

Referential Example 2

The same operation as in Referential Example 1 was performed except that: the monomer concentration of sodium acrylate aqueous solution whose neutralization rate was 75 mol % was 38 mass %, and 7.0 g of trimethylolpropane triacrylate was used as the cross-linking agent instead of polyethylene glycol diacrylate, and a grinding condition of the vibrating mill was changed, thereby obtaining an irregularly crushed water-absorbent resin (b) whose mass average particle diameter was 360 μm.

A surface-cross-linking agent constituted of one mass part of propylene glycol, 0.05 mass parts of ethylene glycol diglycidyl ether, 3 mass parts of water, and one mass part of isopropyl alcohol was mixed with 100 mass parts of the obtained water-absorbent resin (b). The mixture was heated at 210° C. for 45 minutes, thereby obtaining a water-absorbent resin (2). An absorption capacity of the water-absorbent resin (2) was 27 (g/g), and an absorption index under a load thereof was 20 (g/g), and an absorption rate thereof was 50 seconds. Further, a mass average particle diameter of the water-absorbent resin (2) was 360 μm, not largely different from the aforementioned water-absorbent resin.

Referential Example 3

The same reaction and operation as in Referential Example 2 were performed so as to obtain the irregularly crushed water-absorbent resin (b) whose mass average particle diameter was 360 μm. The water-absorbent resin (b) was regarded as the water-absorbent resin (3). An absorption capacity of the water-absorbent resin (3) was 32 (g/g), and an absorption index under a load thereof was 13 (g/g), and an absorption rate thereof was 25 seconds.

Referential Example 4

The same reaction and operation as in Referential Example 2 were performed except that a grinding condition of the vibrating mill was changed, thereby obtaining an irregularly crushed water-absorbent resin (c) whose mass average particle diameter was 440 μm. The water-absorbent resin (c) was regarded as a water-absorbent resin (4). An absorption capacity of the water-absorbent resin (4) was 32 (g/g), and an absorption index under a load thereof was 13 (g/g), and an absorption rate thereof was 53 seconds.

Referential Example 5

The same reaction and operation as in Referential Example 1 were performed so as to obtain the irregularly crushed water-absorbent resin (a) whose mass average particle diameter was 295 μm. The water-absorbent resin (a) was regarded as a water-absorbent resin (5). An absorption capacity of the water-absorbent resin (5) was 45 (g/g), and an absorption index under a load thereof was 9 (g/g), and an absorption rate thereof was 21 seconds.

Referential Example 6

5.9 g of polyethylene glycol diacrylate (average additional molar number of ethylene oxide was 8) was dissolved in 5500 g of sodium acrylate aqueous solution (monomer concentration was 38 mass %) whose neutralization rate was 65 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 90° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified and blended, thereby obtaining an irregularly crushed water-absorbent resin (d). A surface-cross-linking agent constituted of 0.5 mass parts of propylene glycol, 0.3 mass parts of 1,4-butanediol, and 3 mass parts of water was mixed with 100 mass parts of the obtained water-absorbent resin (d). The mixture was heated at 200° C. for 45 minutes, thereby obtaining a water-absorbent resin (6). An absorption capacity of the water-absorbent resin (6) was 31 (g/g), and a diffusing absorption capacity thereof was 30 (g/g), and an amount of particles whose particle diameter was not less than 850 μm was 0 mass %, and an amount of particles whose particle diameter was less than 850 μm and not less than 600 μm was 14 mass %, and an amount of particles whose particle diameter was less than 600 μm and not less than 300 μm was 70 mass %, and an amount of particles whose particle diameter was less than 300 μm and not less than 150 μm was 15 mass %, and an amount of particles whose particle diameter was less than 150 μm was 2 mass %.

Referential Example 7

3.6 g of polyethylene glycol diacrylate (average additional molar number of ethylene oxide was 8) was dissolved in 5500 g of sodium acrylate aqueous solution (monomer concentration was 33 mass %) whose neutralization rate was 60 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 85° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified by the metal gauze which is 20 mesh (850 μm in mesh) and blended, thereby obtaining an irregularly crushed water-absorbent resin (e). A surface-cross-linking agent constituted of 0.5 mass parts of propylene glycol, 0.03 mass parts of ethylene glycol diglycidyl ether, 0.3 mass parts of 1,4-butanediol, and 3 mass parts of water was mixed with 100 mass parts of the obtained water-absorbent resin (e). The mixture was heated at 195° C. for 40 minutes, thereby obtaining a water-absorbent resin (7). An absorption capacity of the water-absorbent resin (7) was 35 (g/g), and a diffusing absorption capacity thereof was 32 (g/g), and an amount of particles whose particle diameter was not less than 850 μm was 0 mass %, and an amount of particles whose particle diameter was less than 850 μm and not less than 600 μm was 17 mass %, and an amount of particles whose particle diameter was less than 600 μm and not less than 300 μm was 65 mass %, and an amount of particles whose particle diameter was less than 300 μm and not less than 150 μm was 16 mass %, and an amount of particles whose particle diameter was less than 150 μm was 1.5 mass %.

Referential Example 8

3.3 g of polyethylene glycol diacrylate (average additional molar number of ethylene oxide was 8) was dissolved in 5500 g of sodium acrylate aqueous solution (monomer concentration was 30 mass %) whose neutralization rate was 55 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 85° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill which is 20 mesh (850 μm in mesh), and was then classified and blended, thereby obtaining an irregularly crushed water-absorbent resin powder (f). A surface-cross-linking agent constituted of 0.5 mass parts of propylene glycol, 0.3 mass parts of 1,4-butanediol, and 3 mass parts of water was mixed with 100 mass parts of the obtained water-absorbent resin powder (f). The mixture was heated at 195° C. for 40 minutes, thereby obtaining water-absorbent resin (8). An absorption capacity of the water-absorbent resin (8) was 34 (g/g), and a diffusing absorption capacity thereof was 31 (g/g), and an amount of particles whose particle diameter was not less than 850 μm was 0.1 mass %, and an amount of particles whose particle diameter was less than 850 μm and not less than 600 μm was 20 mass %, and an amount of particles whose particle diameter was less than 600 μm and not less than 300 μm was 65 mass %, and an amount of particles whose particle diameter was less than 300 μm and not less than 150 μm was 14 mass %, and an amount of particles whose particle diameter was less than 150 μm was 0.8 mass %.

Referential Example 9

3.4 g of polyethylene glycol diacrylate (average additional molar number of ethylene oxide was 8) was dissolved in 5500 g of sodium acrylate aqueous solution (monomer concentration was 38 mass %) whose neutralization rate was 75 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 90° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified by the metal gauze which is 20 mesh (850 μm in mesh) and blended, thereby obtaining an irregularly crushed water-absorbent resin powder (g). A surface-cross-linking agent constituted of 0.5 mass parts of propylene glycol, 0.03 mass parts of ethylene glycol diglycidyl ether, 0.3 mass parts of 1,4-butanediol, and 3 mass parts of water was mixed with 100 mass parts of the obtained water-absorbent resin powder (g). The mixture was heated at 210° C. for 55 minutes, thereby obtaining a water-absorbent resin (9). An absorption capacity of the water-absorbent resin (9) was 36 (g/g), and a diffusing absorption capacity thereof was 32 (g/g), and an amount of particles whose particle diameter was not less than 850 μm was 0 mass %, and an amount of particles whose particle diameter was less than 850 μm and not less than 600 μm was 16 mass %, and an amount of particles whose particle diameter was less than 600 μm and not less than 300 μm was 58 mass %, and an amount of particles whose particle diameter was less than 300 μm and not less than 150 μm was 22 mass %, and an amount of particles whose particle diameter was less than 150 μm was 4 mass %.

Referential Example 10

3.1 g of polyethylene glycol diacrylate (average additional molar number of ethylene oxide was 8) was dissolved in 5500 g of sodium acrylate aqueous solution (monomer concentration was 33 mass %) whose neutralization rate was 65 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 85° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified and blended by a metal gauze which is 20 mesh (850 μm in mesh), thereby obtaining an irregularly crushed water-absorbent resin powder (h). A surface-cross-linking agent constituted of 0.5 mass parts of propylene glycol, 0.03 mass parts of ethylene glycol diglycidyl ether, 0.3 mass parts of 1,4-butanediol, and 3 mass parts of water was mixed with 100 mass parts of the obtained water-absorbent resin powder (h). The mixture was heated at 195° C. for 60 minutes, thereby obtaining a water-absorbent resin (10). An absorption capacity of the water-absorbent resin (10) was 42 (g/g), and a diffusing absorption capacity thereof was 12 (g/g), and an amount of particles whose particle diameter was not less than 850 μm was 0 mass %, and an amount of particles whose particle diameter was less than 850 μm and not less than 600 μm was 3 mass %, and an amount of particles whose particle diameter was less than 600 μm and not less than 300 μm was 52 mass %, and an amount of particles whose particle diameter was less than 300 μm and not less than 150 μm was 37 mass %, and an amount of particles whose particle diameter was less than 150 μm was 8 mass %.

Referential Example 11

6.8 g of polyethylene glycol diacrylate (average additional molar number of ethylene oxide was 8) was dissolved in 5500 g of sodium acrylate aqueous solution (monomer concentration was 20 mass %) whose neutralization rate was 30 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction liquid kept at 30° C. Next, while stirring the reaction solution, 2.46 g of sodium persulfate and 0.10 g of L-ascorbic acid were added to the reaction solution, so that polymerization was initiated approximately one minute later. Then, the polymerization was performed at 30° C. to 80° C. In 60 minutes after the initiation of the polymerization, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 150° C. for 90 minutes. Next, the dried resultant was ground using a vibrating mill, and was then classified and blended by a metal gauze which is 20 mesh (850 μm in mesh), thereby obtaining an irregularly crushed water-absorbent resin powder (i). A surface-cross-linking agent constituted of 0.3 mass parts of propylene glycol, 0.5 mass parts of 1,4-butanediol, and 3 mass parts of water was mixed with 100 mass parts of the obtained water-absorbent resin powder (i). The mixture was heated at 210° C. for 50 minutes, thereby obtaining a water-absorbent resin (11). An absorption capacity of the water-absorbent resin (11) was 22 (g/g), and a diffusing absorption capacity thereof was 18 (g/g), and an amount of particles whose particle diameter was not less than 850 μm was 0 mass %, and an amount of particles whose particle diameter was less than 850 μm and not less than 600 μm was 13 mass %, and an amount of particles whose particle diameter was less than 600 μm and not less than 300 μm was 70 mass %, and an amount of particles whose particle diameter was less than 300 μm and not less than 150 μm was 16 mass %, and an amount of particles whose particle diameter was less than 150 μm was 2 mass %.

Referential Example 12

5.3 g of polyethylene glycol diacrylate (average additional molar number of ethylene oxide was 8) was dissolved in 6600 g of sodium acrylate aqueous solution (monomer concentration was 35.5 mass %) whose neutralization rate was 68 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 3.23 g of sodium persulfate and 0.016 g of L-ascorbic acid were added to the reaction solution, so that polymerization was initiated approximately one minute later. Then, the polymerization was performed at 30° C. to 90° C. When 40 minutes passed after the polymerization had been initiated, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 170° C. for 40 minutes. Next, the dried resultant was ground using a vibrating mill, and was then classified and blended by a metal gauze which is 20 mesh (850 μm in mesh), thereby obtaining an irregularly crushed water-absorbent resin powder (j). A surface-cross-linking agent constituted of 0.51 mass parts of propylene glycol, 0.31 mass parts of 1,4-butanediol, and 2.73 mass parts of water was mixed with 100 mass parts of the obtained water-absorbent resin powder (j). The mixture was heated at 200° C. for 40 minutes, thereby obtaining a water-absorbent resin (12). An absorption capacity of the water-absorbent resin (12) was 33 (g/g), and a diffusing absorption capacity thereof was 30 (g/g), and an amount of particles whose particle diameter was not less than 850 μm was 0.1 mass %, and an amount of particles whose particle diameter was less than 850 μm and not less than 600 μm was 23 mass %, and an amount of particles whose particle diameter was less than 600 μm and not less than 300 μm was 60 mass %, and an amount of particles whose particle diameter was less than 300 μm and not less than 150 μm was 15 mass %, and an amount of particles whose particle diameter was less than 150 μm was 2.0 mass %.

Referential Example 13

5.6 g of polyethylene glycol diacrylate (average additional molar number of ethylene oxide was 8) was dissolved in 6600 g of sodium acrylate aqueous solution (monomer concentration was 38 mass %) whose neutralization rate was 70 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 3.44 g of sodium persulfate and 0.017 g of L-ascorbic acid were added to the reaction solution, so that polymerization was initiated approximately one minute later. Then, the polymerization was performed at 30° C. to 90° C.

When 40 minutes passed after the polymerization had been initiated, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 170° C. for 40 minutes. Next, the dried resultant was ground using a vibrating mill, and was then classified and blended by a metal gauze which is 20 mesh (850 μm in mesh), thereby obtaining an irregularly crushed water-absorbent resin powder (j). A surface-cross-linking agent constituted of 0.51 mass parts of propylene glycol, 0.31 mass parts of 1,4-butanediol, and 2.73 mass parts of water was mixed with 100 mass parts of the obtained water-absorbent resin powder (j). The mixture was heated at 200° C. for 50 minutes, thereby obtaining a water-absorbent resin (13). An absorption capacity of the water-absorbent resin (13) was 32 (g/g), and a diffusing absorption capacity thereof was 30 (g/g), and an amount of particles whose particle diameter was not less than 850 μm was 0.1 mass %, and an amount of particles whose particle diameter was less than 850 μm and not less than 600 μm was 20 mass %, and an amount of particles whose particle diameter was less than 600 μm and not less than 300 μm was 62 mass %, and an amount of particles whose particle diameter was less than 300 μm and not less than 150 μm was 16 mass %, and an amount of particles whose particle diameter was less than 150 μm was 2.0 mass %.

Referential Example 14

5.6 g of polyethylene glycol diacrylate (average additional molar number of ethylene oxide was 8) was dissolved in 6600 g of sodium acrylate aqueous solution (monomer concentration was 38 mass %) whose neutralization rate was 72 mol % so as to generate a reaction solution. Next, the reaction solution was deaerated in a nitrogen gas atmosphere for 30 minutes. Next, the reaction solution was placed in a reaction vessel which is a 10 L double-arm kneader of stainless steel with two sigma type vanes and a jacket, completed with a lid. Then, nitrogen gas exchange was performed with a temperature of the reaction solution kept at 30° C. Next, while stirring the reaction solution, 3.42 g of sodium persulfate and 0.017 g of L-ascorbic acid were added to the reaction solution, so that polymerization was initiated approximately one minute later. Then, the polymerization was performed at 30° C. to 90° C. When 40 minutes passed after the polymerization had been initiated, hydrous gelatinous polymer was obtained. The obtained hydrous gelatinous polymer was segmentalised so that a diameter thereof was approximately 5 mm. The segmentalised hydrous gelatinous polymer was spread on a metal gauze which is 50 mesh (300 μm in mesh), and was dried with hot air at 170° C. for 40 minutes. Next, the dried resultant was ground using a vibrating mill, and was then classified and blended by a metal gauze which is 20 mesh (850 μm in mesh), thereby obtaining an irregularly crushed water-absorbent resin powder (j). A surface-cross-linking agent constituted of 0.51 mass parts of propylene glycol, 0.31 mass parts of 1,4-butanediol, and 2.73 mass parts of water was mixed with 100 mass parts of the obtained water-absorbent resin powder (j). The mixture was heated at 200° C. for 50 minutes, thereby obtaining a water-absorbent resin (14). An absorption capacity of the water-absorbent resin (14) was 33 (g/g), and a diffusing absorption capacity thereof was 30 (g/g), and an amount of particles whose particle diameter was not less than 850 μm was 0.1 mass %, and an amount of particles whose particle diameter was less than 850 μm and not less than 600 μm was 23 mass %, and an amount of particles whose particle diameter was less than 600 μm and not less than 300 μm was 58 mass %, and an amount of particles whose particle diameter was less than 300 μm and not less than 150 μm was 17 mass %, and an amount of particles whose particle diameter was less than 150 μm was 2.0 mass %.

Example 1

As a semi-fermented tea extract and/or a fermented tea extract, 0.5 mass parts of pooal tea extract was mixed with 100 mass parts of the water-absorbent resin (1), obtained in Referential Example 1, whose surface had been treated, thereby obtaining a water-absorbent composition (1). The pooal tea extract was obtained as follows: 50 g of "Pooal Tea" (sold by UJINOTSUYUSEICHA Co., Ltd. located in Kamikoma Higashitsukurimichi 50 Yamashiro-cho Soraku-gun Kyoto Japan) was ground into not more than 500 μm, and was put in 500 g of water. Thereafter, extraction was performed by stirring the water at approximately 80° C. for an hour. Thus obtained extract was filtered, thereby obtaining the pooal tea extract. The properties and deodorant effects of the water-absorbent composition (1) are shown in Table 1. Further, the deodorant effects of the absorbing product containing the water-absorbent composition (1) are shown in Table 1.

Example 2

As a semi-fermented tea extract and/or a fermented tea extract, 0.5 mass parts of oolong tea extract ("Oolong Tea, Oolong Tea Extract A-15" made by Takasago International Corporation, located in Nishiyahata 1-4-11, Hiratsuka-shi, Kanagawa, Japan) was mixed with 100 mass parts of the water-absorbent resin (1), obtained in Referential Example 1, whose surface had been treated, thereby obtaining a water-absorbent composition (2). The properties and deodorant effects of the water-absorbent composition (2) are shown in Table 1. Further, the deodorant effects of the absorbing product containing the water-absorbent composition (2) are shown in Table 1.

Example 3

As a semi-fermented tea extract and/or a fermented tea extract, 0.5 mass parts of oolong tea extract was mixed with 100 mass parts of the water-absorbent resin (1), obtained in Referential Example 1, whose surface had been treated, thereby obtaining a water-absorbent composition (3). The oolong tea extract was obtained as follows: 50 g of "Oolong Tea" (made by Uji-En Co. Ltd. located in Mikagenakamachi 1-2-22, Higashinada-ku, Kobe-shi, Hyogo, Japan) was ground into not more than 500 μm, and put in 500 g of water. Thereafter, extraction was performed by stirring the water at approximately 80° C. for an hour. Thus obtained extract was filtered, thereby obtaining the oolong tea extract. The properties and the deodorant effect of the water-absorbent composition (3) are shown in Table 1. The deodorant effect of the absorbing product (3) having the water-absorbent composition (3) is shown in Table 1.

Example 4

As a semi-fermented tea extract and/or a fermented tea extract, 1.0 mass part of red tea extract was mixed with 100 mass parts of the water-absorbent resin (1), obtained in Referential Example 1, whose surface had been treated, and 1.0 mass part of ion exchange water was mixed in the mixture. Thereafter, 0.3 mass parts of silicon dioxide (AEROSIL 200, produced by Nippon Aerosil Co., Ltd.) as inorganic powder was added to the mixture, thereby obtaining a water-absorbent composition (4). The red tea extract was obtained as follows: 50 g of "Tea: Nittoh Kocha (Nittoh Tea)" (made by MITSUI NORIN. CO., LTD. located in Nishishinjyuku 3-2-11, Shinjyuku-ku, Tokyo, Japan) was ground into not more than 500 μm, and put in 500 g of water. Thereafter, extraction was performed by stirring the water at approximately 80° C. for an hour. Thus obtained extract was filtered, thereby obtaining the red tea extract. The properties and the deodorant effect of the water-absorbent composition (4) are shown in Table 1. The deodorant effect of the absorbing product (4) having the water-absorbent composition (4) is shown in Table 1.

Example 5

As a semi-fermented tea extract and/or a fermented tea extract, 0.5 mass parts of pooal tea extract was mixed with 100 mass parts of the water-absorbent resin (2), obtained in Referential Example 2, whose surface had been treated, and 1.0 mass part of ion exchange water was mixed in the mixture. Thereafter, 0.3 mass parts of silicon dioxide (AEROSIL 200, produced by Nippon Aerosil Co., Ltd.) as inorganic powder was added to the mixture, thereby obtaining a water-absorbent composition (5). The pooal tea extract was obtained as follows: 50 g of "Pooal Tea (sold by UJINOTSUYUSEICHA Co., Ltd. located in Kamikoma Higashitsukurimichi 50 Yamashiro-cho Soraku-gun Kyoto Japan) was ground into not more than 500 μm, and put in 500 g of water. Thereafter, extraction was performed by stirring the water at approximately 80° C. for an hour. Thus obtained extract was filtered, thereby obtaining the pooal tea extract. The properties and the deodorant effect of the water-absorbent composition (5) are shown in Table 1. The deodorant effect of the absorbing product (5) having the water-absorbent composition (5) is shown in Table 1.

Example 6

As a semi-fermented tea extract and/or a fermented tea extract, 1.0 mass part of oolong tea extract was mixed with 100 mass parts of the water-absorbent resin (2), obtained in Referential Example 2, whose surface had been treated, thereby obtaining a water-absorbent composition (6). The oolong tea extract was obtained as follows: 50 g of "Oolong Tea" (made by Uji-En Co., Ltd. located in Mikagenakamachi 1-2-22, Higashinada-ku, Kobe-shi, Hyogo, Japan) was ground into not more than 50 μm, and put in 500 g of water. Thereafter, extraction was performed by stirring the water at approximately 80° C. for an hour. Thus obtained extract was filtered, thereby obtaining the oolong tea extract. The properties and the deodorant effect of the water-absorbent composition (6) are shown in Table 1. The deodorant effect of the absorbing product (6) having the water-absorbent composition (6) is shown in Table 1.

Example 7

As a semi-fermented tea extract and/or a fermented tea extract, 1.0 mass part of red tea extract was mixed with 100 mass parts of the water-absorbent resin (2), obtained in Referential Example 2, whose surface had been treated, thereby obtaining the water-absorbent composition (7). The red tea extract was obtained as follows: 50 g of "Tea: Brooke Bond Tea (Quick Brew Extract)" (made by Nippon Kocha Co., Ltd. located in Nihonbashi Kabuto-cho 21-7, Chuo-ku, Tokyo, Japan) was ground into not more than 500 μm, and put in 500 g of water. Thereafter, extraction was performed by stirring the water at approximately 80° C. for an hour. Thus obtained extract was filtered, thereby obtaining the red tea extract. The properties and the deodorant effect of the water-absorbent composition (7) are shown in Table 1. The deodorant effect of the absorbing product (7) having the water-absorbent composition (7) is shown in Table 1.

Comparative Example 1

The water-absorbent resin (1), obtained in Referential Example 1, whose surface had been treated, was regarded as a compared water-absorbent composition (1). Table 1 shows properties and deodorant effects of the compared water-absorbent composition (1). Table 1 also shows deodorant effects of a compared absorbing product (1) including the compared water-absorbent composition (1).

Comparative Example 2

0.5 mass parts of a commercial deodorant (Flavonoid-B made by Daiichi Kasei industry Co., Ltd) constituted of green tea extract was mixed with 100 mass parts of the water-absorbent resin (1), obtained in Referential Example 1, whose surface had been treated, thereby obtaining a compared water-absorbent composition (2). Table 1 shows properties and deodorant effects of the compared water-absorbent composition (2). Table 1 also shows deodorant effects of a compared absorbing product (2) including the compared water-absorbent composition (2).

Comparative Example 3

As a semi-fermented tea extract and/or a fermented tea extract, 0.5 mass parts of pooal tea extract was mixed with 100 mass parts of the water-absorbent resin (3), obtained in Referential Example 3, thereby obtaining a compared water-absorbent composition (3). The pooal tea extract was obtained as follows: 50 g of "Pooal Tea" (sold by UJINOTSUYUSEICHA Co., Ltd. located in Kamikoma Higashitsukurimichi 50 Yamashiro-cho Soraku-gun Kyoto Japan) was ground into not more than 500 μm, and put in 500 g of water. Thereafter, extraction was performed by stirring the water at approximately 80° C. for an hour. Thus obtained extract was filtered, thereby obtaining the pooal tea extract. Table 1 shows properties and deodorant effects of the compared water-absorbent composition (3). Table 1 also shows deodorant effects of a compared absorbing product (3) including the compared water-absorbent composition (3).

Comparative Example 4

As a semi-fermented tea extract and/or a fermented tea extract, 0.5 mass parts of red tea extract was mixed with 100 mass parts of the water-absorbent resin (4), obtained in Referential Example 4, thereby obtaining a compared water-absorbent composition (4). The red tea extract was obtained as follows: 50 g of "Tea: Lipton YELLOW LABEL" (sold by NIIPON LEVER Co., Ltd. located in Shibuya 2-22-3, Shibuya-ku, Tokyo, Japan) was ground into not more than 500 μm, and put in 500 g of water. Thereafter, extraction was performed by stirring the water at approximately 80° C. for an hour. Thus obtained extract was filtered, thereby obtaining the red tea extract. Table 1 shows properties and deodorant effects of the compared water-absorbent composition (4). Table 1 also shows deodorant effects of a compared absorbing product (4) including the compared water-absorbent composition (4).

Comparative Example 5

As a semi-fermented tea extract and/or a fermented tea extract, 1.0 mass part of pooal tea extract was mixed with 100 mass parts of the water-absorbent resin (5), obtained in Referential Example 5, thereby obtaining a compared water-absorbent composition (5). The pooal tea extract was obtained as follows: 50 g of "Pooal Tea" (sold by UJINOTSUYUSEICHA Co., Ltd. located in Kamikoma Higashitsukurimichi 50 Yamashiro-cho Soraku-gun Kyoto Japan) was ground into not more than 500 μm, and put in 500 g of water. Thereafter, extraction was performed by stirring the water at approximately 80° C. for an hour. Thus obtained extract was filtered, thereby obtaining the pooal tea extract. Table 1 shows properties and deodorant effects of the compared water-absorbent composition (5). Table 1 also shows deodorant effects of a compared absorbing product (5) including the compared water-absorbent composition (5).

Comparative Example 6

As a semi-fermented tea extract and/or a fermented tea extract, 1.0 mass part of oolong tea extract was mixed with 100 mass parts of the water-absorbent resin (5), obtained in Referential Example 5, thereby obtaining a compared water-absorbent composition (6). The oolong tea extract was obtained as follows: 50 g of "Oolong Tea" (made by Uji-En Co., Ltd. located in Mikagenakamachi 1-2-22, Higashinada-ku, Kobe-shi, Hyogo, Japan) was ground into not more than 500 μm, and put in 500 g of water. Thereafter, extraction was performed by stirring the water at approximately 80° C. for an hour. Thus obtained extract was filtered, thereby obtaining the oolong tea extract. Table 1 shows properties and deodorant effects of the compared water-absorbent composition (6). Table 1 also shows deodorant effects of a compared absorbing product (6) including the compared water-absorbent composition (6).

Comparative Example 7

As a semi-fermented tea extract and/or a fermented tea extract, 1.0 mass part of oolong tea extract was mixed with 100 mass parts of Noniolex NA-150M (made by Showa Denko K. K.: the absorption rate is 23 (g/g), the absorption index under a load is 7(g/g), and the absorption rate is 65 (seconds)) which is a water-absorbent resin, thereby obtaining a compared water-absorbent composition (7). The oolong tea extract was obtained as follows: 50 g of "Oolong Tea" (made by Uji-En Co., Ltd. located in Mikagenakamachi 1-2-22, Higashinada-ku, Kobe-shi, Hyogo, Japan) was ground into not more than 500 μm, and put in 500 g of water. Thereafter, extraction was performed by stirring the water at approximately 80° C. for an hour. Thus obtained extract was filtered, thereby obtaining the oolong tea extract. Table 1 shows properties and deodorant effects of the compared water-absorbent composition (7). Table 1 also shows deodorant effects of a compared absorbing product (7) including the compared water-absorbent composition (7).

TABLE 1

| | | | SEMI-FERMENTED TEA EXTRACT AND/OR FERMENTED TEA EXTRACT TYPE | WATER-ABSORBENT COMPOSITION | | | | | | |
|---|---|---|---|---|---|---|---|---|---|---|
| | | | | ABSORPTION CAPACITY (g/g) | ABSORPTION INDEX UNDER LOAD (g/g) | ABSORPTION RATE (SECOND) | DEODRANT TEST-A | | | ABSORBENG PRODUCT DEODRANT TEST-C |
| | | WATER-ABSORBENT RESIN | WATER-ABSORBENT COMPOSITION | | | | INITIAL STAGE | 3 HOURS LATER | 6 HOURS LATER | |
| EXAMPLES | 1 | WATER-ABSORBENT RESIN (1) | WATER-ABSORBENT COMPOSITION (1) | POOAL TEA EXTRACT | 33 | 21 | 37 | 24 | 2.9 | 3.2 | 2.4 |
| | 2 | WATER-ABSORBENT RESIN (1) | WATER-ABSORBENT COMPOSITION (2) | COLONG TEA EXTRACT | 33 | 21 | 37 | 24 | 2.8 | 3.0 | 2.5 |
| | 3 | WATER-ABSORBENT RESIN (1) | WATER-ABSORBENT COMPOSITION (3) | COLONG TEA EXTRACT | 33 | 21 | 37 | 25 | 2.8 | 3.1 | 2.5 |
| | 4 | WATER-ABSORBENT RESIN (1) | WATER-ABSORBENT COMPOSITION (4) | RED TEA EXTRACT | 32 | 19 | 37 | 24 | 2.6 | 3.0 | 2.3 |
| | 5 | WATER-ABSORBENT RESIN (2) | WATER-ABSORBENT COMPOSITION (5) | POOAL TEA EXTRACT | 27 | 18 | 50 | 26 | 2.9 | 3.3 | 2.2 |
| | 6 | WATER-ABSORBENT RESIN (2) | WATER-ABSORBENT COMPOSITION (6) | COLONG TEA EXTRACT | 27 | 20 | 50 | 24 | 2.7 | 3.2 | 2.1 |
| | 7 | WATER-ABSORBENT RESIN (2) | WATER-ABSORBENT COMPOSITION (7) | RED TEA EXTRACT | 27 | 20 | 50 | 25 | 2.7 | 3.3 | 2.2 |
| COMPARATIVE EXAMPLES | 1 | WATER-ABSORBENT RESIN (1) | COMPARED WATER-ABSORBENT COMPOSITION (1) | — | 33 | 21 | 37 | 4.0 | 4.3 | 5.0 | 4.0 |
| | 2 | WATER-ABSORBENT RESIN (1) | COMPARED WATER-ABSORBENT COMPOSITION (2) | GREEN TEA EXTRACT | 33 | 21 | 37 | 3.3 | 3.6 | 4.0 | 3.8 |
| | 3 | WATER-ABSORBENT RESIN (3) | COMPARED WATER-ABSORBENT COMPOSITION (3) | POOAL TEA EXTRACT | 32 | 13 | 25 | 3.5 | 3.7 | 4.1 | 4.0 |
| | 4 | WATER-ABSORBENT RESIN (4) | COMPARED WATER-ABSORBENT COMPOSITION (4) | RED TEA EXTRACT | 32 | 13 | 53 | 3.6 | 3.9 | 4.2 | 3.9 |
| | 5 | WATER-ABSORBENT RESIN (5) | COMPARED WATER-ABSORBENT COMPOSITION (5) | POOAL TEA EXTRACT | 45 | 9 | 21 | 3.7 | 3.8 | 4.3 | 4.2 |
| | 6 | WATER-ABSORBENT RESIN (5) | COMPARED WATER-ABSORBENT COMPOSITION (6) | COLONG TEA EXTRACT | 45 | 9 | 21 | 3.6 | 4.0 | 4.2 | 4.2 |
| | 7 | NONOLEX | COMPARED WATER-ABSORBENT COMPOSITION (7) | COLONG TEA EXRACT | 23 | 7 | 65 | 3.7 | 4.0 | 4.3 | 4.3 |

Example 8

1.0 mass parts of 15 mass % aqueous solution of a theaceous plant leaf extract containing polyphenol and caffeine (commercial name: FS-80MO made by SHIRAIMATSU PHARMACEUTICAL CO., LTD. located in 3-7-1 Ugawa, Mizuguchi-cho, Koga-gun, Shiga, Japan) was added and mixed to 100 mass parts of the water-absorbent resin (6) obtained in Referential Example 6, thereby obtaining a water-absorbent composition (8). Table 2 shows the absorption capacity, the diffusing absorption capacity, the particle size distribution, and the deodorant effect of the water-absorbent composition (8).

Example 9

The same operation as in Example 8 was performed except that the water-absorbent resin (7) obtained in Referential Example 7 was used instead of the water-absorbent resin (6) used in Example 8, thereby obtaining a water-absorbent resin composition (9). Table 2 shows the absorption capacity, the diffusing absorption capacity, the particle size distribution, and the deodorant effect of the water-absorbent composition (9).

Example 10

The same operation as in Example 8 was performed except that the water-absorbent resin (8) obtained in Referential Example 8 was used instead of the water-absorbent resin (6) used in Example 8, thereby obtaining a water-absorbent resin composition (10). Table 2 shows the absorption capacity, the diffusing absorption capacity, the particle size distribution, and the deodorant effect of the water-absorbent composition (10).

Example 11

The same operation as in Example 8 was performed except that the water-absorbent resin (12) obtained in Referential Example 12 was used instead of the water-absorbent resin (6) used in Example 8, thereby obtaining a water-absorbent resin composition (11). Table 2 shows the absorption capacity, the diffusing absorption capacity, the particle size distribution, and the deodorant effect of the water-absorbent composition (11).

Example 12

The same operation as in Example 8 was performed except that the water-absorbent resin (13) obtained in Referential Example 13 was used instead of the water-absorbent resin (6) used in Example 8, thereby obtaining a water-absorbent resin composition (12). Table 2 shows the absorption capacity, the diffusing absorption capacity, the particle size distribution, and the deodorant effect of the water-absorbent composition (12).

Example 13

The same operation as in Example 8 was performed except that the water-absorbent resin (14) obtained in Referential Example 14 was used instead of the water-absorbent resin (6) used in Example 8, thereby obtaining a water-absorbent resin composition (13). Table 2 shows the absorption capacity, the diffusing absorption capacity, the particle size distribution, and the deodorant effect of the water-absorbent composition (13).

Example 14

As a semi-fermented tea extract and/or a fermented tea extract, 1.0 mass parts of red tea extract was added and mixed to 100 mass parts of the water-absorbent resin (7) obtained in Referential Example 7, thereby obtaining a water-absorbent resin composition (14). The red tea extract was obtained as follows: 50 g of "Tea: Lipton YELLOW LABEL" (sold by NIPPON LEVER, Shibuya 2-22-3, Shibuya-ku, Tokyo, Japan) was ground into not more than 500 μm, and put in 500 g of water. Thereafter, extraction was performed by stirring the water at approximately 80° C. for an hour. Thus obtained extract was filtered, thereby obtaining the red tea extract. Table 2 shows the absorption capacity, the diffusing absorption capacity, the particle size distribution, and the deodorant effect of the water-absorbent composition (14).

Example 15

As a semi-fermented tea extract and/or a fermented tea extract, 1.0 mass parts of oolong tea extract ("Oolong Tea, Oolong Tea Extract A-15" made by Takasago International Corporation, located in Nishiyahata 1-4-11, Hiratsuka-shi, Kanagawa, Japan) was added and mixed to 100 mass parts of the water-absorbent resin (7) obtained in Referential Example 7, thereby obtaining a water-absorbent resin composition (15). Table 2 shows the absorption capacity, the diffusing absorption capacity, the particle size distribution, and the deodorant effect of the water-absorbent composition (15).

Example 16

As a semi-fermented tea extract and/or a fermented tea extract, 1.0 mass parts of pooal tea extract was added and mixed to 100 mass parts of the water-absorbent resin (7), obtained in Referential Example 7, thereby obtaining a water-absorbent resin composition (16). The pooal tea extract was obtained as follows: 50 g of "Pooal Tea" (sold by UJINOTSUYUSEICHA Co., Ltd. located in Kamikoma Higashitsukurimichi 50 Yamashiro-cho Soraku-gun Kyoto Japan) was ground into not more than 500 μm, and put in 500 g of water. Thereafter, extraction was performed by stirring the water at approximately 80° C. for an hour. Thus obtained extract was filtered, thereby obtaining the pooal tea extract. Table 2 shows the absorption capacity, the diffusing absorption capacity, the particle size distribution, and the deodorant effect of the water-absorbent resin composition (16).

Example 17

As a semi-fermented tea extract and/or a fermented tea extract, 1.0 mass parts of red tea extract was added and mixed to 100 mass parts of the water-absorbent resin (14) obtained in Referential Example 14, thereby obtaining a compared water-absorbent resin composition (17). The red tea extract was obtained as follows: 50 g of "Tea: Lipton YELLOW LABEL" (sold by NIPPON LEVER, located in Shibuya 2-2-3, Shibuya-ku, Tokyo, Japan) was ground into not more than 500 μm, and put in 500 g of water. Thereafter, extraction was performed by stirring the water at approximately 80° C. for an hour. Thus obtained extract was filtered, thereby obtaining the red tea extract. Table 2 shows the absorption capacity, the diffusing absorption capacity, the particle size distribution, and the deodorant effect of the water-absorbent resin composition (17).

Example 18

As a semi-fermented tea extract and/or a fermented tea extract, 1.0 mass parts of oolong tea extract ("Oolong Tea, Oolong Tea Extract A-15" made by Takasago International Corporation, located in Nishiyahata 1-4-11, Hiratsuka-shi, Kanagawa, Japan) was added and mixed to 100 mass parts of the water-absorbent resin (14) obtained in Referential Example 14, thereby obtaining a water-absorbent resin composition (18). Table 2 shows the absorption capacity, the diffusing absorption capacity, the particle size distribution, and the deodorant effect of the water-absorbent resin composition (18).

Example 19

As a semi-fermented tea extract and/or a fermented tea extract, 1.0 mass parts of pooal tea extract was added and mixed to 100 mass parts of the water-absorbent resin (14) obtained in Referential Example 14, thereby obtaining a water-absorbent resin composition (19). The pooal tea extract was obtained as follows: 50 g of "Pooal Tea" (sold by UJI-NOTSUYUSEICHA Co., Ltd. located in Kamikoma Higashi-itsukurimichi 50 Yamashiro-cho Soraku-gun Kyoto Japan) was ground into not more than 500 μm, and put in 500 g of water. Thereafter, extraction was performed by stirring the water at approximately 80° C. for an hour. Thus obtained extract was filtered, thereby obtaining the pooal tea extract. Table 2 shows the absorption capacity, the diffusing absorption capacity, the particle size distribution, and the deodorant effect of the water-absorbent resin composition (19).

Example 20

The same operation as in Example 14 was performed except that the water-absorbent resin (9) obtained in Referential Example 9 was used instead of the water-absorbent resin (7) used in Example 14, thereby obtaining a water-absorbent resin composition (20). Table 2 shows the absorption capacity, the diffusing absorption capacity, the particle size distribution, and the deodorant effect of the water-absorbent composition (20).

Example 21

The same operation as in Example 15 was performed except that the water-absorbent resin (9) obtained in Referential Example 9 was used instead of the water-absorbent resin (7) used in Example 15, thereby obtaining a water-absorbent resin composition (21). Table 2 shows the absorption capacity, the diffusing absorption capacity, the particle size distribution, and the deodorant effect of the water-absorbent composition (21).

Example 22

The same operation as in Example 8 was performed except that: 20 mass % ethanol solution of theaceous plant leaf extract containing polyphenol and caffeine (commercial name: FS1000 made by SHIRAIMATSU PHARMACEUTICAL CO., LTD. located in 3-7-1 Ugawa, Mizuguchi-cho, Koga-gun, Shiga, Japan) was used instead of 15 mass % aqueous solution of theaceous plant leaf extract containing polyphenol and caffeine, thereby obtaining a water-absorbent resin composition (22). Table 2 shows the absorption capacity, the diffusing absorption capacity, the particle size distribution, and the deodorant effect of the water-absorbent resin composition (22).

Example 23

The same operation as in Example 8 was performed except that: 4 mass % ethanol solution of theaceous plant leaf extract containing polyphenol and caffeine (commercial name: Fresh E made by SHIRAIMATSU PHARMACEUTICAL CO., LTD. located in 3-7-1 Ugawa, Mizuguchi-cho, Koga-gun, Shiga, Japan) was used instead of 15 mass % aqueous solution of theaceous plant leaf extract containing polyphenol and caffeine, thereby obtaining a water-absorbent resin composition (23). Table 2 shows the absorption capacity, the diffusing absorption capacity, the particle size distribution, and the deodorant effect of the water-absorbent resin composition (23).

Example 24

The same operation as in Example 8 was performed except that: 20 mass % aqueous solution of theaceous plant leaf extract containing polyphenol and caffeine (commercial name: FS-500M made by SHIRAIMATSU PHARMACEUTICAL CO., LTD. located in 3-7-1 Ugawa, Mizuguchi-cho, Koga-gun, Shiga, Japan) was used instead of 15 mass % aqueous solution of theaceous plant leaf extract containing polyphenol and caffeine, thereby obtaining a water-absorbent resin composition (24). Table 2 shows the absorption capacity, the diffusing absorption capacity, the particle size distribution, and the deodorant effect of the water-absorbent resin composition (24).

Example 25

1 mass part of 15 mass % aqueous solution of theaceous plant leaf extract containing polyphenol and caffeine (commercial name: FS-80MO made by SHIRAIMATSU PHARMACEUTICAL CO., LTD. located in 3-7-1 Ugawa, Mizuguchi-cho, Koga-gun, Shiga, Japan) was added and mixed to 100 mass parts of the water-absorbent resin (6) obtained in Referential Example 6, and 1.0 mass parts of ion exchange water was mixed thereto. Thereafter, 0.3 mass parts of silicon dioxide (AEROSIL 200, produced by Nippon Aerosil Co., Ltd.) as inorganic powder was added, thereby obtaining a water-absorbent resin composition (25). Table 2 shows the absorption capacity, the diffusing absorption capacity, the particle size distribution, and the deodorant effect of the water-absorbent resin composition (25).

Comparative Example 8

The same operation as in Example 8 was performed except that the water-absorbent resin (9) obtained in Referential Example 9 was used instead of the water-absorbent resin (6) used in Example 8, thereby obtaining a compared water-absorbent resin composition (8). Table 2 shows the absorption capacity, the diffusing absorption capacity, the particle size distribution, and the deodorant effect of the compared water-absorbent resin composition (8).

Comparative Example 9

The same operation as in Example 8 was performed except that the water-absorbent resin (10) obtained in Referential Example 10 was used instead of the water-absorbent resin (6) used in Example 8, thereby obtaining a compared water-absorbent resin composition (9). Table 2 shows the absorption capacity, the diffusing absorption capacity, the particle size distribution, and the deodorant effect of the compared water-absorbent resin composition (9).

Comparative Example 10

The same operation as in Example 8 was performed except that the water-absorbent resin (11) obtained in Referential Example 11 was used instead of the water-absorbent resin (6) used in Example 8, thereby obtaining a compared water-absorbent resin composition (10). Table 2 shows the absorption capacity, the diffusing absorption capacity, the particle size distribution, and the deodorant effect of the compared water-absorbent resin composition (10).

Example 26

25 mass parts of the water-absorbent resin composition (8) obtained in Example 8 and 75 mass parts of crushed wood pulp were mixed in a drying manner using a mixer. Next, the obtained mixture was deposited, in an airy-formation manner, on a wire screen which is 400 mesh (38 μm in mesh), using a batch type airy formation device, so as to form a web of 120 mm×400 mm. Further, this web was pressed at a pressure of 196.14 kPa for five seconds, thereby obtaining an absorbent body whose scale was approximately 0.05 g/cm².

Next, a back sheet (liquid-impermeable sheet), made of liquid-impermeable polypropylene, the absorbent, and an nonwoven surface sheet (liquid-permeable sheet) made of liquid-permeable polypropylene were made to adhere to each other in this order using double face tapes, thereby obtaining an absorbing product (that is, a pad-type adult paper diaper) (8). Mass of the absorbing product (8) was 50 g. A returning amount, a diffusing area of liquid, and a deodorant test result of the absorbing product (8) are shown in Table 3.

Examples 27, 28, 29, 30, 31, 32, 33, 34, and 35

The water-absorbent resin composition (8) obtained in Examples 26 was changed to the water-absorbent resin compositions (9), (10), (11), (12), (13), (14), (15), (17), and (18) obtained in Examples 9, 10, 11, 12, 13, 14, 15, 17, and 18, thereby obtaining absorbing products (9), (10), (11), (12), (13), (14), (15), (16), and (17). The returning amounts, the diffusing areas of liquid, and the deodorant test results of the obtained absorbing products (9), (10), (11), (12), (13), (14), (15), (16), and (17) are shown in Table 3.

Comparative Examples 11, 12, and 13

The water-absorbent resin composition (8) obtained in Examples 26 was changed to the compared water-absorbent resin compositions (8), (9), and (10) obtained in Comparative Examples 8, 9, and 10, thereby obtaining compared absorbing products (8), (9), and (10). The returning amounts, the diffusing areas of liquid, and the deodorant test results of the compared absorbing products (8), (9), and (10) are shown in Table 3.

TABLE 2

| | | NEUTRALIZATION RATE | WATER-ABSORBENT COMPOSITION | 850 μm on (MASS %) | 850 μm pass 600 μm on (MASS %) | 600 μm pass 300 μm on (MASS %) | 300 μm pass 150 μm on (MASS %) | 150 μm pass (MASS %) | ABSORPTION CAPACITY (g/g) | DIFFUSING ABSORPTION CAPACITY (g/g) | DEODORANT TEST-B |
|---|---|---|---|---|---|---|---|---|---|---|---|
| EXAMPLES | 8 | 65 | WATER-ABSORBENT COMPOSITION (8) | 0 | 15 | 72 | 13 | 0.4 | 30 | 29 | 3.1 |
| | 9 | 60 | WATER-ABSORBENT COMPOSITION (9) | 0 | 19 | 63 | 17 | 1 | 35 | 32 | 2.4 |
| | 10 | 55 | WATER-ABSORBENT COMPOSITION (10) | 0 | 22 | 63 | 14 | 1 | 34 | 30 | 2.6 |
| | 11 | 68 | WATER-ABSORBENT COMPOSITION (11) | 0 | 23 | 60 | 15 | 2 | 33 | 30 | 3.1 |
| | 12 | 70 | WATER-ABSORBENT COMPOSITION (12) | 0 | 21 | 60 | 17 | 2 | 32 | 30 | 3.1 |
| | 13 | 72 | WATER-ABSORBENT COMPOSITION (13) | 0 | 24 | 57 | 17 | 2 | 33 | 30 | 3.2 |
| | 14 | 60 | WATER-ABSORBENT COMPOSITION (14) | 0 | 19 | 63 | 17 | 1 | 35 | 32 | 2.4 |
| | 15 | 60 | WATER-ABSORBENT COMPOSITION (15) | 0 | 19 | 63 | 17 | 1 | 35 | 32 | 2.5 |
| | 16 | 60 | WATER-ABSORBENT COMPOSITION (16) | 0 | 19 | 63 | 17 | 1 | 35 | 32 | 2.4 |
| | 17 | 72 | WATER-ABSORBENT COMPOSITION (17) | 0 | 24 | 57 | 17 | 2 | 33 | 29 | 3.1 |
| | 18 | 72 | WATER-ABSORBENT COMPOSITION (18) | 0 | 24 | 57 | 17 | 2 | 33 | 29 | 3 |
| | 19 | 72 | WATER-ABSORBENT COMPOSITION (19) | 0 | 24 | 57 | 17 | 2 | 33 | 29 | 3.2 |
| | 20 | 75 | WATER-ABSORBENT COMPOSITION (20) | 0 | 16 | 59 | 22 | 3 | 35 | 25 | 3.5 |
| | 21 | 75 | WATER-ABSORBENT COMPOSITION (21) | 0 | 16 | 59 | 22 | 3 | 35 | 25 | 3.3 |
| | 22 | 65 | WATER-ABSORBENT COMPOSITION (22) | 0 | 15 | 72 | 13 | 0.4 | 30 | 29 | 2.9 |
| | 23 | 65 | WATER-ABSORBENT COMPOSITION (23) | 0 | 15 | 72 | 13 | 0.4 | 30 | 29 | 2.9 |
| | 24 | 65 | WATER-ABSORBENT COMPOSITION (24) | 0 | 15 | 72 | 13 | 0.4 | 30 | 29 | 3.1 |
| | 25 | 65 | WATER-ABSORBENT COMPOSITION (25) | 0 | 15 | 59 | 22 | 3 | 35 | 27 | 2.8 |
| COMPARATIVE EXAMPLES | 8 | 75 | COMPARED WATER-ABSORBENT COMPOSITION (8) | 0 | 16 | 52 | 38 | 7 | 35 | 25 | 4.0 |
| | 9 | 65 | COMPARED WATER-ABSORBENT COMPOSITION (9) | 0 | 3 | 69 | 17 | 1 | 42 | 12 | 4.2 |
| | 10 | 30 | COMPARED WATER-ABSORBENT COMPOSITION (10) | 0 | 13 | | | | 22 | 18 | 4.8 |

TABLE 3

| | | NEUTRALIZATION RATE | ABSORBING PRODUCT | 850 μm on (MASS %) | 850 μm pass 600 μm on (MASS %) | 600 μm pass 300 μm on (MASS %) | 300 μm pass 150 μm on (MASS %) | 150 μm pass (MASS %) | RETURNING AMOUNT (g) | DIFFUSING AREA OF LIQUID (%) | DEODORANT TEST-D |
|---|---|---|---|---|---|---|---|---|---|---|---|
| EXAMPLES | 26 | 65 | ABSORBING PRODUCT (8) | 0 | 15 | 72 | 13 | 0.4 | 2 | 100 | 2.8 |
| | 27 | 60 | ABSORBING PRODUCT (9) | 0 | 19 | 63 | 17 | 1 | 1 | 100 | 2.3 |
| | 28 | 55 | ABSORBING PRODUCT (10) | 0 | 22 | 63 | 14 | 1 | 2 | 100 | 2.4 |
| | 29 | 68 | ABSORBING PRODUCT (11) | 0 | 23 | 60 | 15 | 2 | 2 | 100 | 2.8 |
| | 30 | 70 | ABSORBING PRODUCT (12) | 0 | 21 | 60 | 17 | 2 | 3 | 100 | 2.8 |
| | 31 | 72 | ABSORBING PRODUCT (13) | 0 | 24 | 57 | 17 | 2 | 3 | 100 | 3 |
| | 32 | 60 | ABSORBING PRODUCT (14) | 0 | 19 | 63 | 17 | 1 | 1 | 100 | 2 |
| | 33 | 60 | ABSORBING PRODUCT (15) | 0 | 19 | 63 | 17 | 1 | 1 | 100 | 2 |
| | 34 | 72 | ABSORBING PRODUCT (16) | 0 | 24 | 57 | 17 | 2 | 3 | 100 | 2.5 |
| | 35 | 72 | ABSORBING PRODUCT (17) | 0 | 24 | 57 | 17 | 2 | 3 | 100 | 2.6 |
| COMPARATIVE EXAMPLES | 11 | 75 | COMPARED ABSORBING PRODUCT (8) | 0 | 16 | 59 | 22 | 3 | 8 | 90 | 3.7 |
| | 12 | 65 | COMPARED ABSORBING PRODUCT (9) | 0 | 3 | 52 | 38 | 7 | 13 | 70 | 4 |
| | 13 | 30 | COMPARED ABSORBING PRODUCT (10) | 0 | 13 | 69 | 17 | 1 | 15 | 100 | 4.7 |

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

What is claimed is:

1. A water-absorbent composition, being particulate, which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol %, wherein
   (1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and
   (2) a plant component (B) selected from the group consisting of oolong tea extract, red tea extract, and theaceous-plant leaf extract containing polyphenols and caffeine is included, the amount of plant component (B) being within a range of preferably from 0.001 to 10 mass parts, with respect to 100 mass parts of the water-absorbent resin;
   wherein an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g; and
   wherein the composition comprises a second monomer other than acrylic acid and salt, and the ratio of the second monomer is not more than 30 mole % with respect to the total amount of the monomer including acrylic acid and salt.

2. The water-absorbent composition as set forth in claim 1, wherein the plant component (B) is selected from plant extracts contained in an aqueous plant.

3. The water-absorbent composition as set forth in claim 1, comprising inorganic fine particles each having a particle diameter of not less than 1 nm and not more than 100 μm.

4. The water-absorbent composition as set forth in claim 1, wherein the water-absorbent resin (A) has a surface portion and/or a periphery thereof which is treated by a cross-linking agent.

5. A process for producing a water-absorbent composition, being particulate, which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol % wherein
   (1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and
   (2) a plant component (B) selected from the group consisting of oolong tea extract, red tea extract, and theaceous-plant leaf extract containing polyphenols and caffeine is included, the amount of plant component (B) being within a range of preferably from 0.001 to 10 mass parts, with respect to 100 mass parts of the water-absorbent resin,
   (3) an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g, and
   (4) the composition comprises a second monomer other than acrylic acid and salt, and the ratio of the second monomer is not more than 30 mole % with respect to the total amount of the monomer including acrylic acid and salt;

said process comprising the steps of:

polymerizing the unsaturated monomer containing sodium acrylate, so as to obtain the water-absorbent resin having the cross-linking structure;

adjusting a particle size of thus obtained water-absorbent resin so that the amount of the particles whose particle diameter is less than 850 μm and not less than 150 μm is not less than 90 mass % with respect to the whole; and mixing the water-absorbent resin whose particle size has been adjusted with the plant component (B).

6. An absorbent, comprising a water-absorbent composition, wherein
   the water-absorbent composition is a particulate water-absorbent composition which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol % wherein
   (1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole,
   (2) a plant component (B) selected from the group consisting of oolong tea extract, red tea extract, and theaceous-plant leaf extract containing polyphenols and caffeine is included, the amount of plant component (B) being within a range of preferably from 0.001 to 10 mass parts, with respect to 100 mass parts of the water-absorbent resin,
   (3) an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g, and
   wherein the composition comprises a second monomer other than acrylic acid and salt, and the ratio of the second monomer is not more than 30 mole % with respect to the total amount of the monomer including acrylic acid and salt.

7. The absorbent as set forth in claim 6, comprising a hydrophilic fiber.

8. The absorbent as set forth in claim 6, wherein the water-absorbent resin (A) has a surface portion and/or a periphery thereof which is treated by a cross-linking agent.

9. An absorbent, comprising:
   a water-absorbent composition, being particulate, which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol %; and a hydrophilic fiber, wherein
said water-absorbent composition is such that:
(1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and
said absorbent further includes (2) a plant component (B) selected from the group consisting of oolong tea extract, red tea extract, and theaceous-plant leaf extract containing polyphenols and caffeine, the amount of plant component (B) being within a range of preferably from 0.001 to 10 mass parts, with respect to 100 mass parts of the water-absorbent resin;
wherein an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g; and
wherein the composition comprises a second monomer other than acrylic acid and salt, and the ratio of the second monomer is not more than 30 mole % with respect to the total amount of the monomer including acrylic acid and salt.

10. An absorbing product, comprising:
an absorbent;
a surface sheet having liquid permeability; and
a back sheet having liquid impermeability, wherein
the absorbent includes a water-absorbent composition, being particulate, which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol %, wherein
said water-absorbent composition is such that:
(1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and
said absorbent further includes (2) a plant component (B) selected from the group consisting of oolong tea extract, red tea extract, and theaceous-plant leaf extract containing polyphenols and caffeine, the amount of plant component (B) being within a range of preferably from 0.001 to 10 mass parts, with respect to 100 mass parts of the water-absorbent resin,
wherein an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g, and
wherein the composition comprises a second monomer other than acrylic acid and salt, and the ratio of the second monomer is not more than 30 mole % with respect to the total amount of the monomer including acrylic acid and salt.

11. The absorbing product as set forth in claim 10, wherein the absorbent includes a hydrophilic fiber.

12. The absorbent as set forth in claim 10, wherein the water-absorbent resin (A) has a surface portion and/or a periphery thereof which is treated by a cross-linking agent.

13. An absorbing product, comprising:
an absorbent;
a surface sheet having liquid permeability; and
a back sheet having liquid impermeability, wherein
the absorbent includes a water-absorbent composition, being particulate, which contains not less than 70 mass % of a water-absorbent resin (A) formed by surface-cross-linking a gelatinous polymer having a cross-linking structure obtained by polymerizing an unsaturated monomer containing sodium acrylate whose acid group neutralization rate is 55-75 mol %; and
a hydrophilic fiber, wherein
said water-absorbent composition is such that:
(1) an amount of particles whose particle diameter is less than 850 μm and not less than 150 μm is not less than 90 mass % with respect to the whole, and an amount of particles whose particle diameter is not less than 300 μm is not less than 60 mass % with respect to the whole, and
said absorbent further includes (2) a plant component (B) selected from the group consisting of oolong tea extract, red tea extract, and theaceous-plant leaf extract containing polyphenols and caffeine, the amount of plant component (B) being within a range of preferably from 0.001 to 10 mass parts, with respect to 100 mass parts of the water-absorbent resin,
wherein an absorption capacity in case where 0.90 mass % of physiological saline is absorbed without load for 60 minutes is not less than 30 g/g, and a diffusing absorption capacity in case where 0.90 mass % of physiological saline is absorbed at 1.9 kPa for 60 minutes is not less than 24 g/g, and
wherein the composition comprises a second monomer other than acrylic acid and salt, and the ratio of the second monomer is not more than 30 mole % with respect to the total amount of the monomer including acrylic acid and salt.

* * * * *